US007993876B2

(12) United States Patent
Nguyen et al.

(10) Patent No.: US 7,993,876 B2
(45) Date of Patent: Aug. 9, 2011

(54) DNA ENCODING PHOSPHOLIPASES AND METHODS OF USING SAME

(75) Inventors: Khanh Q. Nguyen, Reichelsheim (DE); Volker Marschner, Bickenbach (DE); Kornelia Titze, Mühltal (DE); Bruno Winter, Stuttgart (DE)

(73) Assignee: AB Enzymes GmbH, Darmstadt (DE)

( * ) Notice: Subject to any disclaimer, the term of this patent is extended or adjusted under 35 U.S.C. 154(b) by 0 days.

(21) Appl. No.: 12/311,406

(22) PCT Filed: Sep. 21, 2007

(86) PCT No.: PCT/EP2007/008257
§ 371 (c)(1),
(2), (4) Date: Jun. 8, 2009

(87) PCT Pub. No.: WO2008/040466
PCT Pub. Date: Apr. 10, 2008

(65) Prior Publication Data
US 2010/0003365 A1    Jan. 7, 2010

(30) Foreign Application Priority Data
Oct. 2, 2006 (DE) .................. 10 2006 046 719

(51) Int. Cl.
*C12P 21/06* (2006.01)
(52) U.S. Cl. ......... 435/69.1; 435/6; 435/7.1; 435/320.1; 435/352; 536/23.1; 530/350
(58) Field of Classification Search ................... None
See application file for complete search history.

(56) References Cited

U.S. PATENT DOCUMENTS

| 4,873,192 A | 10/1989 | Kunkel |
| 5,264,367 A | 11/1993 | Aalrust et al. |
| 5,378,623 A | 1/1995 | Hattori et al. |
| 5,521,080 A | 5/1996 | Hattori et al. |
| 5,538,874 A | 7/1996 | Hattori et al. |
| 5,965,422 A | 10/1999 | Loffler et al. |
| 6,140,094 A | 10/2000 | Loffler et al. |
| 6,514,739 B1 * | 2/2003 | Udagawa et al. ............. 435/197 |
| 6,759,225 B2 | 7/2004 | Udagawa et al. |

FOREIGN PATENT DOCUMENTS

| CA | 2136050 | 5/1995 |
| DE | 43 39 556 C1 | 2/1995 |
| EP | 0 513 709 B2 | 11/1992 |
| EP | 0 575 133 A2 | 12/1993 |
| EP | 0 808 903 A2 | 11/1997 |
| EP | 1131416 A1 | 9/2001 |
| JP | 3151879 | 6/1991 |
| JP | 7177884 | 7/1995 |
| JP | 10155493 | 6/1998 |
| WO | WO-91/14772 | 10/1991 |
| WO | WO-98/18912 | 5/1998 |
| WO | WO-98/26057 | 6/1998 |
| WO | WO-98/31790 | 7/1998 |
| WO | WO-00/28044 | 5/2000 |
| WO | WO-00/32758 | 6/2000 |
| WO | WO-01/27251 A1 | 4/2001 |
| WO | WO-01-29222 A2 | 4/2001 |
| WO | WO-02/24881 A1 | 3/2002 |
| WO | WO-02/066622 A2 | 8/2002 |
| WO | WO-03/060112 A1 | 7/2003 |
| WO | WO-03/097825 | 11/2003 |
| WO | WO-2004/097012 A2 | 11/2004 |
| WO | WO-2004/111216 A2 | 12/2004 |

OTHER PUBLICATIONS

Tuddenham et al. (Nucleic Acids Research, vol. 22, No. 17, pp. 3511-3533, 1994).*
D. Shen et al., "Characterisation and expression of phospholipases B from the opportunistic fungus *Aspergillus fumigatus*", FEMS *Microbiology Letters*, 239, pp. 87-93 (2004).
Database Geneseq [online], "*Aspergillus fumigatus* essential gene protein #155", XP002471089 (Nov. 4, 2004).
G. Haki et al., "Developments in inudstrially important thermostable enzymes: a review", *Bioresource Technology*, vol. 89, pp. 17-34 (2003).
S. Hong et al., "Identification and molecular cloning of a gene encoding Phospholipase $A_2$ (*plaA*) from *Aspergillus nidulans*", *Biochimica et Biophysica Acta*, vol. 1735, pp. 222-229 (2005).
A. Memon et al., "Phopholipase B activity in mycelia of *Aspergillus niger*", FEMS *Microbiology Letters*, vol. 18, pp. 15-18 (1983).
W.C. McMurray et al., "Phospholipid Metabolism", Department of Biochemistry, University of Western Ontario, London, Ontario, Canada, Copyright 1972, pp. 129-160.
H. Fyrst et al., "The PLB2 Gene of *Saccharomyces cerevisiae* Confers Resistance to Lysophosphatidylcholine and Encodes a Phospholipase B/Lysophospholipase", *Biochemistry*, vol. 38, pp. 5864-5871 (1999).
N. Masuda et al., "Primary structure of protein moiety of *Penicillium notatum* phospholipase B deduced from the cDNA", *Eur. J. Biochem.*, vol. 202, pp. 783-787 (1991). K.S. Lee et al., "The *Saccharomyces cerevisiae PLB1* Gene Encodes a Protein Required for Lysophospholipase and Phospholipase B Activity", *The Journal of Biological Chemistry*, 269(31), pp. 19725-19730 (1994).
O. Merkel et al., "Characterization and Function in Vivo of Two Novel Phospholipases B/Lysophospholipases from *Saccharomyces cerevisiae*",*The Journal of Biological Chemistry*, 274(40), pp. 28121-28127 (1999).
Y. Watanabe et al., "Cloning and sequencing of phospholipase B gene from the yeast *Torulaspora delbrueckii*", FEMS *Microbiology Letters*, vol. 124, pp. 29-34 (1994).
H. Oishi et al., "Purification and Characterization of Phospholipase B from *Kluyveromyces lactis*, and Cloning of Phospholipase B Gene", *Biosci Biotechnol. Biochem.*, vol. 63, pp. 83-90 (1999).

(Continued)

*Primary Examiner* — Hope Robinson
(74) *Attorney, Agent, or Firm* — Peter F. Corless; Christine C. O'Day; Edwards Angell Palmer & Dodge LLP

(57) ABSTRACT

The invention relates to a DNA sequence that encodes a polypeptide with phospholipase activity and was isolated from *Aspergillus* and sequences derived therefrom, polypeptides with phospholipase activity encoded by these sequences as well as the use of these polypeptides for degumming of vegetable oil, for the preparation of dough and/or bakery products, for the preparation of dairy products, for processing steps in the textile industry and for related applications.

11 Claims, 11 Drawing Sheets

OTHER PUBLICATIONS

S.D. Leidich et al., "Cloning and Disruption of ca*PLB1*, a Phospholipase B Gene Involved in the Pathogenicity of *Candida albicans*", *The Journal of Biological Chemistry*, 273(40), pp. 26078-26086 (1998).

Y. Sugiyama et al., "Molecular cloning of a second phospholipase B gene, *caPLB2* from *Candida albicans*", *Medical Mycology*, vol. 37, pp. 61-67 (1999).

D.S. Hirschberg et al., "A Linear Space Algorithm for Computing Maximal Common Subsequences", *Commun. Assoc. Comput. Mach.*, vol. 18, pp. 341-343 (1975).

E.W. Myers et al., "Optimal alignments in linear space", *CABIOS*, 4(1), pp. 11-17 (1988).

K. Chao et al., "Aligning two sequences within a specified diagonal band", *CABIOS*, 8(5), pp. 481-487 (1992).

T.A. Kunkel et al., "Rapid and efficient site-specific mutagenesis without phenotypic selection", *Proc. Natl. Acad. Sci. USA*, vol. 82, pp. 488-492 (1985).

T.A. Kunkel et al, "Rapid and Efficient Site-Specific Mutagenesis without Phenotypic Selection", *Methods in Enzymology*, vol. 154, pp. 367-382 (1987).

F. Mooi et al., "The Use and Restriction Endonucleases and T4 DNA Ligase", *Techniques in Molecular Biology—MacMillan Publishing Company*, New York, Walker and Gaastra, pp. 199-219 (1983).

M.O. Dayhoff et al., "A Model of Evolutionary Change in Proteins", *Atlas of Protein Sequence and Structure*, Natl. Biomed. Res. Found., Washington, DC, pp. 345-352 (1978).

M. Penttila et al., "A versatile transformation system for the cellulolytic filamentous fungus *Trichoderma reesei*", *Gene*, vol. 61, pp. 155-164 (1987).

* cited by examiner

Figure 5

```
   1 AAGCTTCTCC ACCATCATAT TCATGCTTTT CAGCCCTTTC AGCAATGTGG
  51 TCCGCGGTTC AAACTACGAA TGCTCCAATG CAATCACCT  ATCTATCCTT
 101 CGCGAGGGAT GAGACCAAAT CACATTGTTT CAATCTCCCA AGACTTTGGC
 151 ATGCTTGGCC TTACTGCTGA TCCACCGTCC CAATATGAGA ACCCCTGGCT
 201 AAGGGACACC GCCCCATTTA TTCAAATACC GAATGATGGC TGCCTCACAT
 251 TGGGGTTGGG TAGAGAGAGC GATATTTGAT CTTATTGTCC CCTCTAGCTG
 301 AATCTTACG  CGGATTATAG CGTGAGGTGG CCTCATACGA CCCAAGATGA
                                                        m
 351 AGTCCATCGC AGTGGCGTGC GCTGTCGCCG GCCTATTATT GTCCGGTAGG
      k  s  i   a  v  a   c   a  v  a  g  l  l    l  s
 401 TGAATCGTTC TGCCTTGAAG TGTGGTTCAA ACTAGTCAAA TCCGCCTGCG
 451 AAACTGGTAC TGATGCCGTC GGACTTCAAT AGGTGCGAGT GGTGCTCCAG
                                              g  a  s   g  a  p
 501 AGCCCTTTCA TGGTGAAATC CTACAGCGTG CCCTGCCCAA TGCCCCCGAT
      e  p  f  h  g  e  i   l  q  r   a  l  p   n  a  p  d
 551 GGATACACAC CCAGTACAGT CGGTTGTCCT GCCAGTCGCC CTACCATTCG
      g  y  t   p  s  t   v  g  c  p   a  s  r   p  t  i
 601 CAGTGCCGCA AAGTTGTCGC CCAACGAGAC GTCATGGCTT CAGACGCGTC
      r  s  a  a   k  l  s   p  n  e   t  s  w   l   q  t  r
 651 GAGGCAAGAC TACTTCTGCG ATGAAGGACT TCTTTAGTCA TGTCAAGATT
      r  g  k    t  t  s  a  m  k  d   f  f  s   h  v  k  i
 701 CAAGACTTCG ACGCGGTGGG GTACATTGAC CGCCATTCCA GTAACTCGTC
      q  d  f   d  a  v   g  y  i  d   r  h  s   s  n  s
 751 GGATCTTCCC AATATCGGCA TCGCAATCTC TGGTGGAGGT TATGAGCAT
      s  d  l  p  n  i  g   i  a  i   s  g  g   y  r  a
 801 TGATGAACGG CGCAGGTGCG ATTAAGGCTT TTGATAGTCG TACGCCGAAT
      l  m  n   g  a  g   a   i  k  a  f  d  s   r  t  p  n
 851 TCTACGAGCC CCGGTCAGTT GGGTGGATTG CTGCAGTCAG CCACTTATCT
      s  t  s   p  g  q   l  g  g  l   l  q  s   a  t  y
 901 TTCTGGCCTG AGTGGTGGAT CATGGCTCGT TGGCTCAATC TACATCAACA
      l  s  g  l   s  g  g   s  w  l   v  g  s   i  y  i  n
 951 ACTTTACTAC TATCTCTGCG CTGCAGACAC ACCAAAAGGG CACCGTTTGG
      n  f  t   t  i  s  a   l  q  t   h  q  k   g  t  v  w
1001 CAATTTCAGA ATTCAATATT CGAAGGTCCC GATGGGGGCA GCATTCAGAT
      q  f  q   n  s  i   f  e  g  p   d  g  g   s  i  q
1051 TTTGGATTCA GCATCCTATT ATAAGGACAT CAGCAATGCG GTGTCCGGAA
      i  l  d   s  a  s  y   y  k  d   i  s  n   a  v  s  g
1101 AGGCGGATGC GGGCTACCCA ACTTCCATCA CTGACTACTG GTACTGATAG
      k  a  d   a  g  y   p  t  s  i   t  d  y
1151 TCGTCGGTCT TCTTTGTCGC TACATAACAT GCTGATGATT TCACAGGGGC
                                                      w  g
1201 CGTGCTTTGT CCTACCAGCT GATCAATGCA ACCAACGGTG GTCCTAGCTA
      r  a  l  s  y  q    l  i  n  a   t  n  g   g  p  s
1251 TACATGGTCC TCCATTGCGC TAACCGACAC ATTTCAGCAG GCAGAGATGC
      y  t  w  s   s  i  a   l  t  d   t  f  q  q   a  e  m
1301 CGATGCCTGT AGTTGTTGCA GATGGTCGCT ACCCCGGAGA ACTTATTATC
      p  m  p   v  v  v  a   d  g  r   y  p  g   e  l  i  i
1351 AGCAGCAATG CCACCATCTA TGAATTTAAT CCTTGGGAAT TTGGAACCTT
      s  s  n  a  t  i    y  e  f  n   p  w  e   f  g  t
1401 TGACCCCACA GTTTTTGGAT TTGCCCCTCT TGAGTATCTT GGCACCAAAT
      f  d  p  t   v  f  g   f  a  p   l  e  y  l   g  t  k
1451 TCAATGGAGG CTCAGTTCCG AGTAATGAGA GCTGTGTGCG CGGCTTTGAC
      f  n  g   g  s  v  p   s  n  e   s  c  v   r  g  f  d
1501 AATGCGGGCT TCGTCATGGG TACATCCTCT ACTCTCTTCA ATCAGTTCCT
      n  a  g   f  v  m   g  t  s  s   t  l  f   n  q  f
1551 TCTTCAGATC AACTCTACGG CTTTGCCGGA TTGGCTGAAA TCCATCTTCA
      l  l  q  i   n  s  t   a  l  p   d  w  l  k   s  i  f
1601 CGGACATCCT GAGGGACATC GGCGAAAAGG ATGAGGACAT TGCTCTATAC
      t  d  i   l  r  d  i   g  e  k   d  e  d   i  a  l  y
```

Figure 5 (continued)

```
1651    GCGCCCAACC CATTCTACCA CTATTCCAAC AATACCAACC CCAATGCCCC
         a  p  n    p  f  y    h  y  s  n    n  t  n    p  n  a
1701    TCAATCTGAA CTGGACCTGG TGGACGGTGG TGAAGATCTG CAAAACATAC
         p  q  s  e  l  d  l    v  d  g    g  e  d  l    q  n  i
1751    CGCTGCACCC ATTGATCAG CCAGAGCGTC ATGTCGATGT TATCTTCGCC
         p  l  h.   p  l  i  q    p  e  r    h  v  d    v  i  f  a
1801    GTTGATTCCT CTGCCGATAC CAAGTACAGC TGGCCCAACG GCACTGCCCT
         v  d  s    s  a  d    t  k  y  s    w  p  n    g  t  a
1851    TGTTGCTACT TATGAGCGTA GCCTGAACAC ATCAGGCATC GCTAATGGCA
         l  v  a  t    y  e  r    s  l  n    t  s  g  i    a  n  g
1901    CCTCCTTTCC TGCAATTCCC GATCAGGATA CGTTCGTGAA CGAAGGCCTG
         t  s  f    p  a  i  p    d  q  d    t  f  v    n  e  g  l
1951    AACACTCGAC CCACGTTCTT CGGGTGCAAC AGCTCAAACA TGACGGGCCC
         n  t  r    p  t  f    f  g  c  n    s  s  n    m  t  g
2001    ATCGCCCTTG ATTGTATATC TCCCAAACTA TCCCTACACC GCTTACTCCA
         p  s  p  l    i  v  y    l  p  n    y  p  y  t    a  y  s
2051    ACTTTTCTAC CTTCCAGCCA GACTACACAG AAGAAGAGCG AGATGCTACC
         n  f  s    t  f  q  p    d  y  t    e  e  e    r  d  a  t
2101    ATCCTCAACG GATATGATGT GGTGACAATG GGTAACAGCA CTCGTGATGG
         i  l  n    g  y  d    v  v  t  m    g  n  s    t  r  d
2151    CAACTGGTCA ACCTGCGTTG GCTGTGCCAT CTTGAGTCGG TCTTTCGAAC
         g  n  w  s    t  c  v    g  c  a    i  l  s  r    s  f  e
2201    GCACAAACAC TAATGTGCCG GAAATCTGCA AACAATGTTT CCAGAGGTAT
         r  t  n    t  n  v  p    e  i  c    k  q  c    f  q  r  y
2251    TGCTGGGACG GCTCTATCAA CAACACCACT CCTGCGGTTT ACGAACCGGT
         c  w  d    g  s  i    n  n  t  t    p  a  v    y  e  p
2301    CACGATTTTG GATAGCGCAG GCTCCGGGAT CTTTCCAAGT ATTCTCGCTG
         v  t  i  l    d  s  a    g  s  g    i  f  p  s    i  l  a
2351    CTGCAATGGC TGCTATTGTT GCCTCTTGGA CTATTCTATA GAATTCATTT
         a  a  m    a  a  i  v    a  s  w    t  i  l    -
2401    CGAGAGTTTC GCGAAATGTC TATTTCGGCC TGATTCTATG CTGACTGAGC
2451    TGTATCTACC CGTCACAACT TTTGTCAGAA GCCATGTTTG TCCATTTGGA
2501    AATTTGACGA GCAATATTGT CGTTGGATCT ATCTATCTAT CGCTTTGTAT
2551    CCCTCTTGTA TATAGCTTAT GCACGAAAAT AAAATATCAT GGCCATGACA
2601    TCCCTTCAGG CGCAATCAAT TACATATAAG CTGGGGGTCA TTAAAATGCC
2651    ACGTGACGGT GGGGTCCGAG TGTTGCTATG ACAACATCCA CGTGACTTCT
2701    CAAACAAGAA ACTTAAGCAC AAACGCCGCA GCTCTAGCGG CGGCCAAAC
2751    GCAACAACAA CACATATCTA ATCAACAAGC TAGGTCTTCT TAAGCCACAG
2801    CAAAGCCCCT GCTTGAAAGC TT
```

```
   1  AAGCTTCTCC ACCATCATAT TCATGCTTTT CAGCCCTTTC AGCAATGTGG
  51  TCCGCGGTTC AAACTACGAA TGCTCCAATG GCAATCACCT ATCTATCCTT
 101  CGCGAGGGAT GAGACCAAAT CACATTGTTT CAATCTCCCA AGACTTTGGC
 151  ATGCTTGGCC TTACTGCTGA TCCACCGTCC CAATATGAGA ACCCCTGGCT
 201  AAGGGACACC GCCCCATTTA TTCAAATACC GAATGATGGC TGCCTCACAT
 251  TGGGGTTGGG TAGAGAGAGC GATATTTGAT CTTATTGTCC CCTCTAGCTG
 301  AATCTTCACG CGGATTATAG CGTGAGGTGG CCTCATACGA CCCAAGATGA
 351  AGTCCATCGC AGTGGCGTGC GCTGTCGCCG GCCTATTATT GTCCGGTAGG
 401  TGAATCGTTC TGCCTTGAAG TGTGGTTCAA ACTAGTCAAA TCCGCCTGCG
 451  AAACTGGTAC TGATGCCGTC GGACTTCAAT AGGTGCGAGT GGTGCTCCAG
 501  AGCCCTTTCA TGGTGAAATC CTACAGCGTG CCCTGCCCAA TGCCCCGAT
 551  GGATACACAC CCAGTACAGT CGGTTGTCCT GCCAGTCGCC CTACCATTCG
 601  CAGTGCCGCA AAGTTGTCGC CAACGAGAC GTCATGGCTT CAGACGCGTC
 651  GAGGCAAGAC TACTTCTGCG ATGAAGGACT TCTTTAGTCA TGTCAAGATT
 701  CAAGACTTCG ACGCGGTGGG GTACATTGAC CGCCATTCCA GTAACTCGTC
 751  GGATCTTCCC AATATCGGCA TCGCAATCTC TGGTGGAGGT TATCGAGCAT
 801  TGATGAACGG CGCAGGTGCG ATTAAGGCTT TTGATAGTCG TACGCCGAAT
 851  TCTACGAGCC CCGGTCAGTT GGGTGGATTG CTGCAGTCAG CCACTTATCT
 901  TTCTGGCCTG AGTGGTGGAT CATGGCTCGT TGGCTCAATC TACATCAACA
 951  ACTTTACTAC TATCTCTGCG CTGCAGACAC ACCAAAAGGG CACCGTTTGG
1001  CAATTTCAGA ATTCAATATT CGAAGGTCCC GATGGGGGCA GCATTCAGAT
1051  TTTGGATTCA GCATCCTATT ATAAGGACAT CAGCAATGCG GTGTCCGGAA
1101  AGGCGGATGC GGGCTACCCA ACTTCCATCA CTGACTACTG GTACTGATAG
1151  TCGTCGGTCT TCTTTGTCGC TACATAACAT GCTGATGATT TCACAGGGGC
1201  CGTGCTTTGT CCTACCAGCT GATCAATGCA ACCAACGGTG GTCCTAGCTA
1251  TACATGGTCC TCCATTGCGC TAACCGACAC ATTTCAGCAG GCAGAGATGC
1301  CGATGCCTGT AGTTGTTGCA GATGGTCGCT ACCCCGGAGA ACTTATTATC
1351  AGCAGCAATG CCACCATCTA TGAATTTAAT CCTTGGGAAT TTGGAACCTT
1401  TGACCCCACA GTTTTTGGAT TTGCCCCTCT TGAGTATCTT GGCACCAAAT
1451  TCAATGGAGG CTCAGTTCCG AGTAATGAGA GCTGTGTGCG CGGCTTTGAC
1501  AATGCGGGCT TCGTCATGGG TACATCCTCT ACTCTCTTCA ATCAGTTCCT
1551  TCTTCAGATC AACTCTACGG CTTTGCCGGA TTGGCTGAAA TCCATCTTCA
1601  CGGACATCCT GAGGGACATC GGCGAAAAGG ATGAGGACAT TGCTCTATAC
1651  GCGCCCAACC CATTCTACCA CTATTCCAAC AATACCAACC CCAATGCCCC
1701  TCAATCTGAA CTGGACCTGG TGGACGGTGG TGAAGATCTG CAAAACATAC
1751  CGCTGCACCC ATTGATCCAG CCAGAGCGTC ATGTCGATGT TATCTTCGCC
1801  GTTGATTCCT CTGCCGATAC CAAGTACAGC TGGCCCAACG GCACTGCCCT
1851  TGTTGCTACT TATGAGCGTA GCCTGAACAC ATCAGGCATC GCTAATGGCA
1901  CCTCCTTTCC TGCAATTCCC GATCAGGATA CGTTCGTGAA CGAAGGCCTG
1951  AACACTCGAC CCACGTTCTT CGGGTGCAAC AGCTCAAACA TGACGGGCCC
2001  ATCGCCCTTG ATTGTATATC TCCCAAACTA TCCCTACACC GCTTACTCCA
2051  ACTTTTCTAC CTTCCAGCCA GACTACACAG AAGAAGAGCG AGATGCTACC
2101  ATCCTCAACG GATATGATGT GGTGACAATG GGTAACAGCA CTCGTGATGG
2151  CAACTGGTCA ACCTGCGTTG GCTGTGCCAT CTTGAGTCGG TCTTTCGAAC
2201  GCACAAACAC TAATGTGCCG GAAATCTGCA AACAATGTTT CCAGAGGTAT
2251  TGCTGGGACG GCTCTATCAA CAACACCACT CCTGCGGTTT ACGAACCGGT
2301  CACGATTTTG GATAGCGCAG GCTCCGGGAT CTTTCCAAGT ATTCTCGCTG
2351  CTGCAATGGC TGCTATTGTT GCCTCTTGGA CTATTCTATA GAATTCATTT
2401  CGAGAGTTTC GCGAAATGTC TATTTCGGCC TGATTCTATG CTGACTGAGC
2451  TGTATCTACC CGTCACAACT TTGTCAGAA GCCATGTTTG TCCATTTGGA
2501  AATTTGACGA GCAATATTGT CGTTGGATCT ATCTATCTAT CGCTTTGTAT
2551  CCCTCTTGTA TATAGCTTAT GCACGAAAAT AAAATATCAT GGCCATGACA
2601  TCCCTTCAGG CGCAATCAAT TACATATAAG CTGGGGGTCA TTAAAATGCC
2651  ACGTGACGGT GGGGTCCGAG TGTTGCTATG ACAACATCCA CGTGACTTCT
2701  CAAACAAGAA ACTTAAGCAC AAACGCCGCA GCTCTAGCGG GCGGCCAAAC
2751  GCAACAACAA CACATATCTA ATCAACAAGC TAGGTCTTCT TAAGCCACAG
2801  CAAAGCCCCT GCTTGAAAGC TT
```

Figure 6

```
  1  MKSIAVACAV  AGLLLSGASG  APEPFHGEIL  QRALPNAPDG  YTPSTVGCPA
 51  SRPTIRSAAK  LSPNETSWLQ  TRRGKTTSAM  KDFFSHVKIQ  DFDAVGYIDR
101  HSSNSSDLPN  IGIAISGGGY  RALMNGAGAI  KAFDSRTPNS  TSPGQLGGLL
151  QSATYLSGLS  GGSWLVGSIY  INNFTTISAL  QTHQKGTVWQ  FQNSIFEGPD
201  GGSIQILDSA  SYYKDISNAV  SGKADAGYPT  SITDYWGRAL  SYQLINATNG
251  GPSYTWSSIA  LTDTFQQAEM  PMPVVADGR   YPGELIISSN  ATIYEFNPWE
301  FGTFDPTVFG  FAPLEYLGTK  FNGGSVPSNE  SCVRGFDNAG  FVMGTSSTLF
351  NQFLLQINST  ALPDWLKSIF  TDILRDIGEK  DEDIALYAPN  PFYHYSNNTN
401  PNAPQSELDL  VDGGEDLQNI  PLHPLIQPER  HVDVIFAVDS  SADTKYSWPN
451  GTALVATYER  SLNTSGIANG  TSFPAIPDQD  TFVNEGLNTR  PTFFGCNSSN
501  MTGPSPLIVY  LPNYPYTAYS  NFSTFQPDYT  EEERDATILN  GYDVVTMGNS
551  TRDGNWSTCV  GCAILSRSFE  RTNTNVPEIC  KQCFQRYCWD  GSINNTTPAV
601  YEPVTILDSA  GSGIFPSILA  AAMAAIVASW  TIL
```

Figure 7

DNA ENCODING PHOSPHOLIPASES AND METHODS OF USING SAME

CROSS REFERENCE TO RELATED APPLICATIONS

This application is National Stage Entry of PCT/EP2007/008257, which was filed on Sep. 21, 2007.

The invention refers to new DNA sequences that encode polypeptides with phospholipase activity. The invention also relates to new polypeptides with phospholipase activity. These polypeptides are acid phospholipases with high thermostability. Moreover, the invention relates to use of these phospholipases for the reduction of phosphorus-containing compounds, for example, in the production of edible oils, as well as the use of this phospholipase as bakery improver, animal feed additive, additive in the processing of textile raw materials etc.

Phospholipids such as lecithin and phosphatidyl choline consist of glycerol esterfied with two fatty acids at the terminal (sn-1) position and the middle (sn-2) position of the glycerol and one ester-bound phosphate group at the third position (sn-3). The phosphate group itself may be esterfied with, e.g., amino alcohols. Phospholipases catalyze the hydrolysis of the acyl binding or the ester binding of phospholipids. There are different types of phospholipases differing in their cleavage pattern. Regarding the acyl-cleaving phospholipases, it is distinguished between phospholipases A1 and A2, which hydrolyze the acyl group either at the sn-1 position or at the sn-2 position and produce lysophospholipids along the way. For this reason the remaining fatty acid may be hydrolyzed by the lysophospholipase (LPL). No position selectivity is known for the lysophospholipases.

Phospholipases of type B, which partly hydrolyze both acyl groups virtually simultaneously without the formation of an intermediate to the lysolecithin being observed, are described in literature (FEMS Microbiol. Let. 18 (1983) 15-18; Annu. Rev. Biochem. 41 (1972) 129-160). Such as for, e.g., the PLB1 and PLB3 activity of *Saccharomyces cerevisiae* (Biochemistry May 4, 1999; 38(18):5864-5871), this is often caused by the fact that the enzyme has much more LPL activity than $PLA_n$ activity. Pure lysophospholipases without phospholipase side activity may not separate fatty acids from phospholipids having fatty acids at the positions sn-1 and sn-2.

The above-described phospholipases of type A, the amino acid sequence and/or nucleic acid sequence of which are/is known, can be divided in 2 groups.

a) The group of the phospholipases of type A with a molecular weight of about 30-40 kDa. The following phospholipases from the state of the art are part of this group: WO 98/31790 (AB Enzymes GmbH) discloses that a suitable phospholipase A for degumming of edible oil was found in *Aspergillus niger*. The protein (36 kDa) only shows phospholipase activity after proteolytic cleavage, whereby the two fragments (30+6 kDa) remain connected via disulphide bridges. The enzyme cleaves lecithin into lysolecithin, but it is also able to cleave lysolecithin further, e.g., to phosphatidyl choline. WO 98/26057 discloses a phospholipase A from *Fusarium* sp. with a molecular weight of 29±10 kDa and an isoelectric point between pI 4.5-8. JP-10-155493 A2 discloses a phospholipase A1 from *A. oryzae* (295 aa); WO 02/24881 dislcoses a phospholipase A from the yeast *Zygosascus hellenicus* (407 aa) with an isoelectric point pI of about 4.2, and JP 03151879 discloses a bacterial phospholipase from *Pseudomonas* sp. with a molecular weight of about 30 kDa.

Moreover, EP 0 575 133 A2 (U.S. Pat. Nos. 5,538,874, 5,378,623, 5,521,080) discloses phospholipases A1 from *Aspergillus* with a molecular weight of 30-40 kDa and a pI of 2.8-4.5, however, without indicating sequence information. Furthermore, these patent specifications do not include any details or strategies to obtain the respective DNA by cloning.

b) The group of the phospholipases of type A with a molecular weight of about 60-100 kDa. It comprises: phospholipases from *Hyphozyma*, a yeast-like fungus, described in WO 98/18912, and phospholipases from *Aspergillus niger* as disclosed in WO 03/097825.

Moreover, phospholipases of type B are mentioned in literature. They are lysophospholipases that may additionally show very little phospholipase A activity.

c) The sequences of several enzymes with molecular weights of 45-100 kDa are known. They include the PLB from *Aspergillus niger* (WO 01/27251, WO 03/097825), the PLB from *Aspergillus fumigatus* (Shen et al. FEMS Microbiol Lett. 2004, 239 (1):87-93), the PLB from *Aspergillus oryzae* (WO 01/27251 & WO 01/29222), the PLB from *Fusarium venenatum* and *Fusarium verticillioides* (WO 00/28044), the PLB from *Penicillium notatum*, also referred to as *P. chrysogenum* (N. Masuda et al., Eur. J. Biochem., 202: 783-787 (1991)), the PLB 1-3 from *Saccharomyces cerevisiae* (Lee et al., 1994 J. Biol. Chem. 269: 19725-19730, Merkel et al., 1999 J. Biol. Chem. 274: 28121-28127), the PLB from *Torulaspora delbrueckii* (former designation: *Saccharomyces rosei*) (Watanabe et al., 1994, FEMS Microbiology Letters 124: 29-34), *Kluyveromyces lactis* (Oishi et al., 1999 Biosci. Biotechnol.

Biochem. 63: 83-90), *Neurospora crassa* (EMBL 042791) and *Schizosaccharomyces pombe* (EMBL O13857).

d) Several sequences of enzymes with a molecular weight of 30-40 kDa are known. They include the lysophospholipase from *Aspergillus foetidus*, EP 0 808 903, the PLB from *A. niger*, WO 01/27251 and WO 03/097825, the PLB1 and PLB2 from *Candida albicans* (J. Biol. Chem. 273 (40): 26078-26086, 1998, Medical Mycology 37:61-67, 1998), and the PLB from *Pseudomonas* PS21, JP 03151879.

Furthermore, WO 2004/097012 discloses "core peptides" of known phospholipases A2 with increased phospholipase activity.

WO 00/32758, WO 03/060112 and WO 2004/111216 disclose methods to obtain enzyme variants that show a different lipase activity or phospholipase activity by means of "protein engineering" of known lipases, e.g., from *Thermomyces lanuginosus* and other phospholipases.

WO 02/066622 discloses new genes with high homology to the genes of the *Thermomyces lanuginosus* lipase as well as their use for gene shuffling to produce new lipolytic enzymes.

Phospholipases are used, e.g., for degumming of edible oils. Non-hydratizable phospholipids are thereby made water soluble by phospholipases, and are, thus, gently, cost-efficiently and environmentally friendly removed from the edible oil. The patent EP 0 513 709 B2 (Röhm GmbH/Metallgesellschaft AG, today AB Enzymes GmbH/mg technologies ag) discloses for the first time an effective enzymatic process for degumming. An edible oil that was previously degummed with water is thereby emulsified with an aqueous solution of a phospholipase. After the hydrolysis, the aqueous phase and the cleavage products of the phosphorus-containing compounds contained therein are separated. The enzymatic degumming process was introduced into the edible oil industry as "EnzyMax Process" by the company Lurgi. DE-A43 39 556 discloses as another variant of this process the re-use of the enzyme by separating the enzyme from a used, muddy aqueous phase by addition of tensides or solubilizers and re-using it as extensively mud-free, enzyme-containing solution. Lysophospholipases, enzymes that are only able to cleave lysolecithin, are ineffective in the degumming process.

Phospholipases are also manifoldly used in the food industry and the animal feed industry, e.g., for the preparation of dough, for the preparation of bakery products, for the preparation of dairy products etc. Thus, there is a need for phospholipases that can be versatilely used in technology.

Phospholipases are also used in the textile industry for bioscouring to purify the plant fibre before the further processing steps such as, e.g., the colorization. A mixture of phospholipase together with other enzymes may also be used here. The other enzymes may be selected from the group of cellulases, hemicellulases, pectinases, proteases and oxidoreductases.

Further fields of application of phospholipases are mayonnaise production, treatment of dairy products or their use in leather processing (JP-A 7-177884).

Therefore, the task of providing proteins or polypeptides with improved phospholipase properties was the base for this invention. The new phospholipases are particularly not to show lipase activity relevant in technological processes. The proteins with phospholipase activity are to have an increased thermostability in particular.

Moreover, the proteins with phospholipase activity are to be produced simply, cost-efficiently and commercially. Furthermore, expression constructs according to the invention, which are suitable for the production of the proteins with phospholipase activity, are to be provided.

The aforementioned tasks are solved by a DNA sequence that encodes a polypeptide with phospholipase activity characterized in that the DNA sequence is selected from a) DNA sequences that comprise a nucleotide sequence according to SEQ ID NO: 1, b) DNA sequences that comprise the encoding sequence according to SEQ ID NO: 1, c) DNA sequences that encode the protein sequence according to SEQ ID NO: 2, d) DNA sequences that are encoded by the plasmid B11B1Hind6 with the restriction map according to FIG. 8 and deposited under the accession number DSM 18369, e) DNA sequences that hybridize with one of the DNA sequences according to a), b), c) or d) under stringent conditions, f) DNA sequences that are related to the DNA sequences according to a), b), c), d) or e) due to the degeneracy of the genetic code, and g) complementary strands to the sequences according to a) to f).

The invention also relates to a polypeptide with phospholipase activity, selected from a) a polypeptide that is encoded by the coding part of one of the aforementioned DNA sequences, b) a polypeptide with the sequence according to SEQ ID NO: 2 or a sequence derived therefrom, which may be obtained by substitution, addition, deletion of one or more amino acid(s) therefrom, c) a polypeptide with a sequence that shows at least 92% identity to the amino acids 33 to 633 of SEQ ID NO: 2, d) a polypeptide that is encoded by a nucleic acid sequence that hybridizes under stringent conditions with (i) the nucleotides 530 to 2388 of SEQ ID NO: 1, (ii) the cDNA sequence included in the nucleotides 530 to 2388 of SEQ ID NO: 1, (iii) a partial sequence of (i) or (ii) of at least 100 nucleotides, or (iv) a complementary strand of (i), (ii) or (iii), e) a variant of the polypeptide with SEQ ID NO: 2 comprising a substitution, deletion and/or insertion of one or more amino acid(s), f) allelic variants to the amino acid sequences a) to e).

Furthermore, the invention relates to expression constructs or hosts that are able to express polypeptides with phospholipase activity according to the invention. Moreover, the invention also relates the respective expression plasmids and vectors. Furthermore, the invention relates to processes for degumming of vegetable oil by means of the polypeptides according to the invention as well as the use of the polypeptides according to the invention for applications in the field of food technology, in particular for the preparation of dough, bakery products or dairy products or in animal nutrition and in the processing of textile raw materials, the so-called scouring or bioscouring.

The sequences of phospholipases stated in the above state of the art are expressis verbis excluded from the scope of protection of the invention. The sequences of the proteins with phospholipase activity as well as the respective DNA sequences of the following documents are particularly excluded from the scope of protection of the invention: WO 01/27251, WO 2004/111216, WO 2004/097012, WO 03/060112, WO 02/24881, WO 00/28044, WO 00/32758, WO 03/097825, EP 999 73 065.8 as well as corresponding divisional applications. The exclusion of the sequences refers to these documents in their entirety as well as individually and in any combination.

It was surprisingly found that a DNA sequence that encodes a polypeptide with phospholipase activity that has a high molecular weight and an increased thermostability may be isolated from a strain of the genus *Aspergillus fumigatus*. This phospholipase is an acid phospholipase deriving from a filamentous fungus with a calculated molecular weight of 65 kDa, which is able to hydrolyze at least one of the two fatty acids from lecithin. This enzyme is further characterized in that the protein may be cleaved into two fragments under denaturing conditions. A fragment with 34 kDa or 20 kDa after deglycosylation with N-glycosidase F and a fragment of about 72 kDa (after deglycosylation with N-glycosidase F of 54 kDa) thereby develops. These fragments do not only show N-glycosylation but also O-glycosylation as the comparison with the molecular weight derived from the amino acid sequence shows (18.4 and 46.6 kDa).

Under the conditions of enzymatic degumming of edible oil, this phospholipase does not show any lipase activity relevant for this process and can, thus, be advantageously used in a process for enzymatic degumming of edible oils, since it hydrolyzes no or only not noteworthy portions of triglyceride compounds. Moreover, the phospholipase according to the invention already shows complete phospholipase activity without proteolytic cleavage in contrast to the phospholipases of the state of the art (for example, WO 98/31790). As opposed to the polypeptides with phospholipase activity known from the state of the art, the phospholipases according to the invention have an increased thermostability and can, thus, also be beneficially used in processes of enzymatic degumming at higher temperatures. This is of particular economic interest, since the temperature of the oil does not have to the lowered in the degumming processes first to make enzymatic degumming possible without inactivation of the enzyme, and subsequently the temperature of the oil has to be increased to lower the viscosity of the oil for the centrifugation step for separating the oil phases from the water phases. The increased thermostability of the polypeptides with phospholipase activity according to the invention is also advantageous for other applications in the field of food technology and animal nutrition and in textile processing, respectively.

Phospholipases with a high molecular weight of filamentous fungi encoded by the above-cited sequences have temperature optima of 25° to 55° C. The present enzyme according to the invention also shows 6 h of activity if applied at 65° C. A repeated use of the enzyme during several degumming cycles is also possible at higher temperatures.

The increased thermostability of the phospholipase of the invention was surprising and not obvious on the basis of the phospholipases described in the state of the art. These properties are neither described nor even rendered obvious by any of the naturally occurring phospholipases of filamentous fungi described in the state of the art.

Since there are no publications on thermostable phospholipases of filamentous fungi and, thus, also no indications as to which structural elements (helices, β-sheets, loops) must be especially designed in a phospholipase (existence of ionic interactions via charged amino acids and, if possible, polyvalent ions, disulphide bridges, van-der-Waals interactions, hydrophobic interactions) to guarantee a high thermostability, it was not possible to predict that the detected phospholipase would have these properties.

The genes of the family of "GX" lipases in the broadest sense, the phospholipases and lysophospholipase being also part of them, show that little changes in the sequence strongly influence the properties of the enzyme that is encoded by this sequence. This is shown, e.g., in the application WO 03/060112. This application describes a process for producing variants of lipolytic enzymes. Alterations in the substrate specificity are thereby obtained by random mutagenesis, not by specific, directed mutations. This application also shows that despite high homology in the sequence, the property of the enzyme encoded therefrom may not be predicted. This lacking correlation between DNA sequence and encoded enzyme as well as differences in the codon usage by the individual strands do not allow for a derivation of primers from known sequences to detect new sequences with specific properties such as high thermostability and low lipase activity.

According to another embodiment, the invention relates to a polypeptide with phospholipase activity characterized in that it has a molecular weight in the range of 63 to 76 kDa and may also be present as fragments of 18.4 kDa to 46.6 kDa (unglycosylated), may hydrolyze at least one of the two fatty acids from lecithin, shows no lipase activity, has an increase thermostability and may be isolated from an organism of the genus *Aspergillus*.

Increased thermostability thereby means that the enzyme maintains an activity of at least 80% for at least 6 h at a temperature of 65° C. under the conditions of the oil degumming with a low water content of 1-5%.

The phospholipase sequence according to the invention and SEQ ID NO: 2 were compared to phospholipase sequences of the state of the art. A high matching with the amino acid sequence from *Aspergillus niger* known from WO 03/097825 on the level of the amino acid sequence was found, i.e., the matching was 74%.

The phospholipase sequence according to the invention and SEQ ID NO: 1 was compared to lysophospholipase sequences of the state of the art, since they may partly show very low phospholipase activity; however, they are lysophspholipases by definition. The sequence SEQ ID: 1 shows the highest identity of 91% with the sequence from (Shen et al., FEMS Microbiol. Letters 2004, 239 (1): 87-93) with the accession number AAQ85122 and 76% identity with sequence 8 from U.S. Pat. No. 6,759,225 (WO 01/027251), which is derived from *Aspergillus oryzae*. In spite of the high matching in the amino acid sequence, they are different enzymes. The enzyme according to the invention shows a predominant phospholipase activity; the enzymes from Shen et al. 2004 and U.S. Pat. No. 6,759,225 are referred to as lysophospholipase. Enzyme activity data on their potential phospholipase activity are not available from the mentioned publications.

Thus, the invention also relates to polypeptides with phospholipase activity with a sequence that has at least 92% identity to the sequence according to SEQ ID NO: 1. The invention preferably relates to a polypeptide with phospholipase activity with a sequence that has at least 92% identity to amino acids 33 to 633 of SEQ ID NO: 1. The degree of identity to amino acids 33 to 633 of SEQ ID NO: 1 is preferably at least 95%, more preferred at least 97% and particularly preferred at least 98% provided that the respective sequences show phospholipase activity.

The degree of sequence identity is thereby determined in such a way that the number of residues of the shorter sequence that is involved in the comparison and has a "corresponding" counterpart in the other sequence is determined. For the purposes of the present invention the identity is thereby preferably determined in the usual manner by means of the usual algorithms. According to the invention, only the cDNAs or amino acids of the respective mature proteins are used for the comparison. Similar, preferably identical, sequence counterparts were determined according to the invention as homologue sequences by means of known computer programs. An example of such a program is the program Clone Manager Suite, which includes the program part Align Plus and is distributed by Scientific & Educational Software, Durham, N.C., U.S.A. A comparison between two DNA sequences or amino acid sequences as defined above is thereby carried out under the option local alignment either according to the FastScan—MaxScore method or according to the Needleman-Wunsch method, keeping the default values. The program version "Clone Manager 7 Align Plus 5" with the functions "Compare Two Sequences/Local Fast Scan-Max Score/ Compare DNA sequences" or for amino acids "Compare Two Sequences/Global/Compare sequences as Amino Acids" was particularly used to calculate the identity according to the invention. The algorithms made available by the following sources were thereby used: Hirschberg, D. S. 1975. A linear space algorithm for computing longest common subsequences. Commun Assoc Comput Mach 18:341-343; Myers, E. W. and W. Miller. 1988. Optimal alignments in linear space. CABIOS 4:1, 11-17; Chao, K-M, W. R. Pearson and W. Miller. 1992. Aligning two sequences within a specified diagonal band. CABIOS 8:5, 481-487.

The invention further relates to addition molecules and/or deletion molecules of the aforementioned polypeptides with phospholipase activity. Thus, a polypeptide with phospholipase activity modified according to the invention may be elongated by adding further sequences at the N-terminal and/ or C-terminal end, whereby the thus obtained amino acid sequences have to show phospholipase activity. Hybrid molecules, which have further advantageous properties, may be thereby produced. For example, suspension proteins or their native precursor forms may be added to proteins largely secreted, which further increases secretion efficiency. Moreover, active sequence parts of other enzymes may be added to produce enzymes with multiple specificity. Furthermore, polar and non-polar sequences may be added to influence the solubility properties or the membrane mobility of the thus obtained enzyme in a desired way.

Sequence segments of the polypeptide with phospholipase activity may also be deleted according to the invention, keeping the phospholipase activity. The mutations, elongations and shortenings may be conducted in a way known per se and with methods well known in the state of the art. Shortened polypeptides are often characterized by an increased secretion height compared to the full-length polypeptides. They may also show higher thermostabilities compared to the full-length polypeptide, since they only contain the "compressed core".

The production of such variants is generally known in the state of the art. For example, amino acid sequence variants of the polypeptides may be produced by mutation in the DNA. Processes for mutagenesis and changes in the nucleotide sequence are well known in the state of the art (cf., for example, Kunkel, Proc. Natl. Acad. Sci. USA, 82:488 (1985), Kunkel et al., Methods in Enzymol., 154:367 (1987), U.S. Pat. No. 4,873,192, Walker und Gaastra, eds., Techniques in Molecular Biology, Mac Millan Publishing Company, New York (1983)). Details on appropriate amino acid substitutions that do not negatively influence the biological activity of the protein of interest can be found in the model by Dayhoff et al., Atlas of Protein Sequence and Structure, Natl. Biomed. Res. Found., Washington, D.C. (1978). Conservative substitutions such as the replacement of an amino acid by another with similar properties are preferred. These replacements may be divided into two main groups with altogether four subgroups, and a replacement in each subgroup is referred to as negative replacement, which does preferably not influence the activity or the folding of the protein.

| aliphatic | non-polar | G A P |
| | | I L V |
| | polar and uncharged | C S T M N Q |
| | polar and charged | D E |
| | | K R |
| aromatic | | H F W Y |

The expressions "protein", "peptide" and "polypeptide" are primarily used interchangeably. A polypeptide or enzyme with phospholipase activity or a phospholipase is to refer to an enzyme that catalyzes the release of fatty acids from phospholipids, for example, lecithins. The phospholipase activity may be determined by use of any assay known per se and using one of these substrates.

In connection with the polypeptides according to the invention the expressions "phospholipase" or phospholipase A are to refer to enzymes with phospholipase A1 activity as well as phospholipase A2 activity. Phospholipase A1 or A2 is thereby defined according to the standard enzyme EC classification as EC 3.1.1.2 or 3.1.1.4. Phospholipase B or lysophospholipase are polypeptides according to the standard enzyme EC classification EC 3.1.1.5.

The invention also relates to DNA sequences that encode a polypeptide with phospholipase activity, comprising mutations, modifications or variations of the sequence according to SEQ ID NO: 1. Furthermore, the invention also relates to sequences that hybridize with the aforementioned sequences under relaxed or stringent conditions. The following conditions are considered as stringent: hybridization at 65° C., 18 h in dextran sulphate solution (GenescreenPlus, DuPont), subsequently washing of the filter for 30 min each, first with 6×SSC, twice 2×SSC, twice 2×SSC, 0.1% SDS and finally with 0.2×SSC at 65° C. (membrane transfer and detection methods, Amersham).

Furthermore, the invention also relates to DNA sequences that are related to the above sequences according to the invention due to the degeneracy of the genetic code as well as allelic variants thereof. The degeneracy of the genetic code may thereby result from the natural degeneracy or an especially selected codon usage. Naturally occurring allelic variants may be identified by means of well-known techniques of molecular biology such as, for example, the polymerase chain reaction (PCR) and hybridization techniques.

The invention also relates to a process for the production of a polypeptide with phospholipase activity using recombinant techniques comprising the growing of recombinant prokaryotic and/or eukaryotic host cells that comprise a DNA sequence according to the invention under conditions that support the expression of the enzyme as well as the subsequent exploitation of the enzyme. The invention also relates to the use of the polynucleotide sequences according to the invention for the production of probes to detect similar sequences that encode respective enzymes in other organisms as well as for the transformation of host cells.

A DNA sequence that encodes a polypeptide according to the invention may be used to transform any host cells such as, for example, cells of fungi, yeasts, bacteria, plants or mammals. Cells transformed in such a way are characterized by a secretion of the phospholipase according to the invention. The thus produced phospholipase enzyme results in an efficient hydrolysis of the fatty acids from phospholipids.

The invention also relates to expression cassettes that may be used to introduce a DNA sequence encoding a phospholipase according to the invention or an open reading frame into a host cell. They preferably comprise a transcription start region that is connected with the open reading frame. Such an expression cassette may comprise a variety of restriction cleavage sites for inserting the open reading frame and/or other DNAs, e.g., a transcription regulator region and/or selectable marker genes. The transcription cassette comprises in 5'→3' direction of the transcription a transcription start region and a translation start region, the DNA sequence of interest and a transcription stop region and translation stop region that is functional in a microbial cell. The termination region may be native regarding the transcription initiation region, may be native regarding the DNA sequence of interest and may be derived from any other source.

The expression "open reading frame" (ORF) refers to the amino acid sequence that is encoded between the translation start codons and translation stop codons of a coding sequence. The expressions "start codon" and "stop codon" refer to a unit of three contiguous nucleotides (codons) in a coding sequence, specifying the chain start and chain stop of the protein synthesis (mRNA translation).

In connection with a nucleic acid "operative linkage" refers to a compound as a part of the same nucleic acid molecule in an appropriate position to and orientation on the transcription start of the promoter. DNA in functional connection to a promoter is located under the transcription initiation regulation of the promoter. Coding sequences may be operatively linked with the regulator sequence in sense orientation or antisense orientation. Regarding polypeptides, operative linkage means the connection as part of the same polypeptide, i.e., via peptide bindings.

According to the invention, any promoter may be used. Promoter usually refers to the nucleotide sequence upstream (5') to the coding sequence and controls the expression of the coding sequence by providing the recognition of the RNA polymerase and other factors that are necessary for the correct transcription. The promoter used according to the invention may comprise a minimal promoter, i.e., a short DNA sequence from a TATA box and other sequences that specify the transcription start site to which regulator elements are attached for expression control.

The promoter used according to the invention may also comprise a nucleotide sequence that comprises a minimal promoter and regulator elements and may control the expression of a coding sequence or functional RNA. This type of promoter sequence consists of proximal and distal elements located upstream, whereby the elements named last are often referred to as enhancers. Consequently, an enhancer is a DNA sequence that may stimulate the promoter activity and may be an element inherent to the promoter or an inserted heterologous element to improve the expression height or tissue specificity of a promoter. It may work in both orientations and may even work if it is located upstream or downstream to the promoter. Not only enhancers but also other upstream located promoter elements sequence-specifically bind DNA-binding proteins mediating their effects. Promoters may be derived from a native gene in their entirety or my be composed of different elements derived from different naturally occurring promoters or can even be composed of synthetic DNA segments. A promoter may also comprise DNA sequences that are involved in the binding of protein factors that control the efficiency of the transcription initiation as response to physiological or development-related conditions.

Promoter elements, particularly TATA elements, that are inactive or have a strongly reduced promoter activity in the absence of an upstream activation are referred to as minimal promoters or core promoters. In the presence of an appropriate transcription factor or appropriate transcription factors the function of the minimal promoter is the enabling of the transcription. Thus, a minimal promoter or core promoter only consists of all basic elements that are necessary for the transcription initiation, e.g., a TATA box and/or an initiator.

The invention also relates to vector constructs comprising DNA sequences according to the invention. These vector constructs comprise any plasmid, cosmid, phage or other vector in double-stranded or single-stranded, linear or circular form, which might also be transmitable or mobilizable themselves and may either transform a prokaryotic or eukaryotic host by integration into the cellular genome or are extra-chromosomally present (e.g., autonomously replicating plasmids with replication origin).

Vectors, plasmids, cosmids, artificial yeast chromosomes (YACs), artificial bacterial chromosomes (BACs) and DNA segments to be used for the transformation of cells generally comprise the DNA that encode the phospholipase according to the invention as well as another DNA such as cDNA, a gene or genes that is/are to be introduced into the cells. These DNA constructs may comprise further structures such as promoters, enhancers, polylinkers or also regulator genes, if necessary. One of the DNA segments or genes that was/were selected for the cellular introduction conveniently codes/code a protein that is expressed in the thus obtained transformed (recombinant) cells, which leads to a screenable or selectable property and/or provides the transformed cell with an improved phenotype.

The construction of vectors that may be used according to the invention is known to a person skilled in the art due to aforementioned disclosure and the general expert knowledge (cf., e.g., Sambrook et al., Molecular Cloning: A Laboratory Manual (2nd ed., Cold Spring Harbor Laboratory Press, Plainview, N.Y. (1989))).

The expression cassette according to the invention may comprise one or several restriction site(s) to put the polynucleotide that encodes the phospholipase under the control of a regulator sequence. The expression cassette may also comprise a termination signal in operative linkage with the polynucleotide as well as regulator sequences that are necessary for the proper translation of the polynucleotide. The expression cassette that comprises the polynucleotide according to the invention may be chimeric, i.e., at least one of its components is heterologous relating to at least one of the other components. The expression of the polynucleotide in the expression cassette may be under control of a constitutive promoter, an inducible promoter, a regulated promoter, a viral promoter or a synthetic promoter.

The vectors may already comprise regulator elements, e.g., promoters, or the DNA sequences according to the invention may be manipulated in such a way that they comprise such elements. Appropriate promoter elements that may be used are known in the state of the art and are, for example, for *Trichoderma reesei* the cbh1 promoter or cbh2 promoter, for *Aspergillus oryzae* the amy promoter, for *Aspergillus niger* the xyl promoter, glaA promoter, alcA promoter, aphA promoter, tpiA promoter, gpdA promoter, sucl promoter and pkiA promoter. Appropriate promoter elements that may be used for expression in yeast are known in the state of the art and are, for example, the pho5 promoter or the gap promoter for expression in *Saccharomyces cerevisiae* and for *Pichia pastoris*, for example, the aoxl promoter or the fmd promoter, or the mox promoter for *H. polymorpha*.

DNA that is appropriate for introduction into cells may also comprise, besides the DNA according to the present invention, DNA that was derived or isolated from any source. An example of a derived DNA is a DNA sequence that was identified in a given organism as a useful fragment and then chemically synthesized in a basically purified form. An example of such a DNA is an appropriate DNA sequence that was, for example, obtained by the use of restriction endonucleases, so that it may be further manipulated according to the invention, for example, amplified. The amdS gene from *Aspergillus nidulans*, which may be used as a marker gene, and its regulatory sequences as well as polylinkers are among those, inter alia.

Such a DNA is usually referred to as recombinant DNA. Thus, an appropriate DNA comprises completely synthetic DNA, semi-synthetic DNA, DNA isolated from biological sources und DNA derived from channelled RNA. Generally, the introduced DNA is no original part of the genotype of the recipient DNA, however, according to the invention, a gene may also be isolated from a given genotype and optionally altered and subsequently multiple copies of the gene may be introduced into the same genotype, e.g., to increase the production of a given gene product.

The introduced DNA comprises without limitation DNA from genes such as, for example, of bacteria, yeasts, fungi or viruses. The channelled DNA may comprise modified or synthetic genes, parts of genes or chimeric genes including genes of the same or a different genotype. For example, DNA of the plasmids pUC18, pUC19 may also be included here.

The DNA used according to the invention for the transformation may be circular or linear, double-stranded or single-stranded. In general, the DNA is a chimeric DNA such as a plasmid DNA, which also comprises coding regions that are flanked by regulator sequences and support the expression of the recombinant DNA present in the transformed cell. For example, the DNA itself may comprise or consist of a promoter that is active in a cell, that is derived from a source differing from the cell, or a promoter that is already present in the cell, i.e., the transformation target cell, may be used.

In general, the introduced DNA is relatively small, less than about 30 kb, to minimize the sensitivity to physical, chemical or enzymatic reduction, which increases with the size of the DNA.

The selection of an appropriate expression vector depends on the host cells. Yeast expression vectors or fungi expression vectors may comprise a replication origin, an appropriate promoter and enhancer as well as any necessary ribosome binding sites, polyadenylation sites, splice donor sites and splice acceptor sites, transcription termination sequence sand non-transcribed 5'-flanking sequences.

Examples of appropriate host cells are: fungi cells of the genus *Aspergillus, Rhizopus, Trichoderma, Neurospora, Mucor, Penicillium* etc. such as, for example, yeasts of the genera *Kluyveromyces, Saccharomyces, Schizosaccharomyces, Trichosporon, Schwanniomyces, Hansenula, Pichia* and the like. Appropriate host systems are, for example, fungi such as *Aspergilli*, e.g., *Aspergillus niger* (ATCC 9142) or *Aspergillus ficuum* (NRLL 3135) or *Trichoderma* (e.g., *Trichoderma reesei* QM6a) and yeasts such as *Saccharomyces*, e.g., *Saccharomyces cerevisiae* or *Pichia* such as, e.g., *Pichia pastoris* or *Hansenula*, e.g., *H. polymorpha* (DSMZ 70277). Such micro-organisms may be obtained from established depositary institutions, e.g., the American Type Culture Collection (ATCC), the Centraalbureau voor Schimmelcultures (CBS) or the Deutschen Sammiung für Mikroorganismen und Zellkulturen GmbH (DSMZ) or any other depositary institution.

The expression cassette may include a transcription start region and translation start region of the polynucleotide according to the invention in the 5'-3' transcription direction and a transcription region and translation region that are functional in vivo or in vitro. The termination region may be native regarding the transcription initiation region or may be native or of other origin regarding the polynucleotide. The regulator sequences may be located upstream (5' non-coding sequences), inwardly (introns) or downstream (3' non-coding sequences) of a coding sequence and influence the transcription, the RNA processing or the stability and/or the translation of the associated coding sequence. Regulator sequences may comprise without limitation enhancers, promoters, repressor binding sites, translation leader sequences, introns or polyadenylation signal sequences. They may comprise natural and synthetic sequences as well as sequences that are combined of synthetic and natural sequences.

The vector used according to the invention may also comprise appropriate sequences for the amplification of the expression.

Examples of promoters that may be used according to the invention are promoters of which is known that they control the expression in the eukaryotic cells. Any promoter with the ability to express in filamentous fungi may be used. Examples are a promoter that is strongly induced by starch or cellulose, e.g., a promoter for glucoamylase or α-amylase from the genus *Aspergillus* or cellulase (cellobiohydrolase) from the genus *Trichoderma*, a promoter for enzymes in the glycolytic metabolic pathway such as, for example, phosphoglycerate kinase (PGK) and glycerol aldehyde-3-phosphate-dehydrogenase (GPD) etc. The cellobiohydrolase-I promoter, the cellobiohydrolase-II promoter, the amylase promoter, the glucoamylase promoter, the xylanase promoter or the enolase promoter is preferred.

In addition to the use of a special promoter, other types of elements may influence the expression of transgenes. It was particularly demonstrated that introns have the potential to increase transgene expression.

The expression cassette may comprise further elements, for example, such elements that may be regulated by endogenous or exogenous elements such as zinc finger proteins, including naturally occurring zinc finger proteins or chimeric zinc finger proteins.

The expression cassette used according to the invention may also comprise enhancer elements or upstream promoter elements.

Vectors for the use according to the invention may be constructed in such a way that they comprise an enhancer element. Thus, the elements according to the invention comprise the gene of interest together with a 3' DNA sequence, which acts as a signal to terminate the transcription and to allow for the polyadenylation of the thus obtained mRNA. Any signal sequence that makes the secretion from the selected host organism possible may be used. A preferred signal sequence is the phospholipase signal sequence from *Aspergillus fumigatus* or signal sequences derived therefrom for the secretion from filamentous fungi.

A special leader sequence may also be used, since the DNA sequence between the transcription start site and the start of the coding sequence, i.e., the non-translated leader sequence, may influence the gene expression. Preferred leader sequences comprise sequences that control the optimal expression of the adhered gene, i.e., they comprise a preferred consensus leader sequence, which increases or maintains the mRNA stability and prevents an inappropriate translation initiation. The selection of such sequences is well known to the person skilled in the art.

To improve the possibility to identify the transformants, a selectable or screenable marker gene may be added to the expression cassette. Such marker genes are well known to a person skilled in the art.

The expression cassette or a vector construct that comprises the expression cassette is introduced into a host cell. A variety of techniques is available and well known to a person skilled in the art of channelling constructs into a host cell. The transformation of microbial cells may be carried out by means of polyethylene glycol, calcium chloride, viral infection, DEAE dextran, phage infection, electroporation and other methods known in the state of the art. The transformation of fungi may be carried out according to Penttiläet al., Gene 61:155-164, 1987. The introduction of a recombinant vector into yeasts may be carried out according to methods known per se, including electroporation, use of spheroplasts, lithium acetate and the like.

As soon as the expression cassette or the DNA sequence according to the invention is obtained, it may be introduced into vectors according to processes known per se to over-express the encoded polypeptide in appropriate host systems. However, DNA sequences as such may also be used to transform appropriate host systems of the invention to obtain an over-expression of the encoded polypeptide.

As soon as a DNA sequence according to the invention is expressed in an appropriate host in an appropriate medium, the encoded phospholipase may be concentrated and/or isolated either from the medium if the phospholipase is secreted into the medium or from the host organism if the phospholipase is intracellularly present, e.g., in the periplasmic space, according to processes known per se. Known processes for the separation of the insoluble parts of the culture medium and the biomass followed by processes for concentrating the phospholipase may be used to produce concentrated phospholipase solutions or to prepare the drying of the phospholipase. For example, filtration processes or centrifugation processes may be used to separate the insoluble components, followed by ultrafiltration processes for concentration, or cross flow filtration processes are used. The drying may be carried out by spray drying, granulation processes, deformation or other processes. Known processes of protein purification may be used to isolate the phospholipases according to the invention. For example, different chromatographic or gel-chromatographic processes may be used individually or in combination. Depending on the host cell used in a recombinant production process, the enzyme according to the invention may or may not be covalently modified by glycosylation. In eukaryotic cells the glycosylation of the secreted proteins provide a basis for modulation of the protein folding, the conformation stability, the thermal stability and the resistance against proteolysis. As regards a specific application of the phospholipase, a glycosylated variant of the enzyme may be preferred to a non-glycosylated variant.

The invention also relates to isolated or basically purified nucleic acid compositions and protein compositions. An isolated and purified polynucleotide/polypeptide or segment thereof refers to a polynucleotide or polypeptide and segment thereof that is isolated from its native environment and is present in a purified form for further use. An isolated polynucleotide segment or polypeptide may be present in a purified form or may be present in a non-native environment such as, for example, in a transgenic host cell. For example, an isolated or purified polynucleotide segment or protein or a biologically active part thereof is basically free from further cellular material or culture medium if produced according to recombinant techniques or is basically free from chemical precursors or other chemical compounds. An isolated polynucleotide is preferably free from sequences (preferably protein-encoding sequences) that naturally flank the nucleic acid (i.e., sequences that are localized at the 5' ends and 3' ends of the nucleic acid) in the genomic DNA of the organism from which the nucleic acid is derived. For example., according to different embodiments, the isolated nucleic acid molecule may comprise less than about 5 kb, 4 kb, 3 kb, 2 kb, 1 kb, 0.5 kb or 0.1 kb of nucleotide sequences that naturally flank the nucleic acid molecule in the genomic DNA of the cell from which the nucleic acid is derived. A protein that is basically free from cellular material comprises compositions of protein and polypeptide with less than about 70%, 50%, 30%, 20%, 10%, 5% (based on the dry weight) of contaminating protein. If the protein according to the invention or a biologically active fragment thereof is recombinantly produced, the culture medium preferably comprises les than about 70%, 50%, 30%, 20%, 10%, 5% (based on the dry weight) of the chemical precursors or non-protein-like chemical substances.

The invention also relates to phospholipase compositions that comprise the polypeptide according to the invention. Phospholipase compositions are generally liquid or dry. Liquid compositions preferably comprise the phospholipase enzyme in a purified or enriched form. However, auxiliary agents such as, for example, a stabilizer and/or glycerol, sorbitol or monopropylene glycol, additives such as salts, sugar, preservatives, agents to adjust the pH value and proteins may be added. Typical liquid compositions are aqueous or oily suspensions.

Dry compositions may be freeze-dried, spray-dried, granulated or extruded compositions, which may only comprise the enzyme. Dry compositions may be granulates that may easily be mixed with, for example, food or feed components,or preferably form a component of a premix. Preferably, the particle size of the enzyme granulate is compatible with the other component of the mixture. This allows for save and purposeful agents to incorporate enzymes in processed food, premixes or animal feed, for example.

Dry compositions may also comprise other additives such as, for example, salts, particularly phosphate salts and their anhydrous forms, and stabilizers such as poly(vinyl pyrrolidone) etc. to regulate certain conditions such as, for example, the pH value in the application.

A food additive according to this embodiment of the present invention may be combined with other food components in a similar way, whereby processed food products are produced. Such other food components comprise one or more enzyme supplements, vitamins, minerals or trace elements. Then the thus obtained combined dietary supplement may be mixed with other food components such as grain and plant proteins in an appropriate amount to obtain processed food. The processing of these components to processed food may be carried out by means of processing devices known per se.

In a preferred embodiment the phospholipase compositions according to the invention additionally comprise an effective amount of one or more enzyme(s) for food or animal feed or for the application in pre-stages of the production of food or animal feed or for the application in the textile industry, preferably selected from alpha-galactosidases, beta-galactosidases, laccases, other phospholipases, phosphatases, endoglucanases, particularly endo-beta-1,4-glucanases, endo-beta-1,3(4)-glucanases, endo-1,2-beta-glucanases and endo-1,3-alpha-glucanases, cellulases, xylosidases, galactanases, particularly arabinogalactan-endo-1,4-beta-galactosidases and arabinogalactan-endo-1,3-beta-galactosidases, pectin-degrading enzymes, particularly pectinases, pectinesterases, pectinlyases, polygalacturonases, arabananases, rhamnogalacturonases, rhamnogalacturonanacetylesterases, rhamnogalacturonan-alpha-rhamnosidases, pectate lyases and alpha-galacturonidases, mannanases, beta-mannosidases, mannan acetylesterases, xylan acetylesterases, proteases, xylanases, arabinoxylanases, lipolytic enzymes such as lipases, digalactosid-diglycerol esterases and cutinases, and other enzymes such as laccases and transglutaminases.

The phospholipases according to the invention may be used for a variety of applications. Examples are applications in baking and in animal feeding as well as in the production of fuels from renewable energy sources, for example, canola seed, or in the processing of textile raw materials.

A preferred application is the use of the polypeptides with phospholipase activity according to the invention in processes for degumming of vegetable oil. The edible oil to be degummed is, for example, treated with a polypeptide according to the invention, whereby the majority of the phospholipids is hydrolyzed, and subsequently the aqueous phase containing the hydrolyzed phospholipids is separated from the oil. Such a process is particularly suitable for the purification of edible oils that contain phospholipids, for example, vegetable oils such as soy bean oil, canola seed oil and sunflower oil.

Before the phospholipase treatment, the oil is preferably pre-treated to eliminate mucilage, for example, by humid refining. Typically, the oil comprises 50 to 850 ppm phosphorus as phospholipid at the beginning of the treatment with the phospholipase according to the invention. After the treatment, the phosphorus value is typically between 2 and 10 ppm.

The phospholipase treatment is generally carried out in such a way that the phospholipase is dispersed in an aqueous solution, preferably as droplets with an average diameter of <10 μm. The amount of water is preferably 0.5 to 5% by weight based on the oil. An emulsifier may optionally be added. It may be mechanically stirred to maintain an emulsion. The treatment with phospholipase may be carried out at a pH value in the range of 3.5 to about 5.0. The pH value of the process may be in the range of about 3.5 to about 5, preferably 3.8 to 4.5 and most preferred 4.0 to 4.2 to maximize the performance of the enzyme. The pH value may be adjusted by, for example, addition of citric acid, a citrate buffer, phosphoric acid or hydrochloric acid. An appropriate temperature is generally 30°-70° C., preferably 45°-65° C. and most preferred 55°-62° C. The reaction time is typically 1 to 12 hours, preferably 2 to 6 hours. An appropriate enzyme dosage is usually 120 to 3,000 units per kg oil, preferably 250 to 2,000 and most preferred 750 to 1,500 units per kg oil.

The phospholipase treatment may be carried out batchwise, for example, in a tank under stirring, or may be continuous, for example, in a number of tank reactors under stirring.

The phospholipase treatment is followed by separation of an aqueous phase and an oily phase. The separation may be carried out by conventional means, for example, centrifugation. The aqueous solution contains phospholipases, and the enzyme may be used again to improve economy of the process.

The treatment may be carried out by means of processes known per se.

Advantageously, the phospholipase according to the invention may also be used to prepare dough and bakery products, whereby an effective amount of a polypeptide according to the invention is incorporated in the dough. By adding a polypeptide with phospholipase activity according to the invention, one or several property(ies) of the dough or the bakery product prepared with the dough may be improved compared to a dough or bakery product without addition of a polypeptide with phospholipase activity according to the invention.

In the dough preparation by means of the phospholipase according to the invention the phospholipase may be added to the dough itself, any ingredient of which the dough is prepared, and/or a mixture of dough ingredients of which the dough is prepared. A polypeptide with phospholipase activity according to the invention may, thus, be added as such in any step of the dough preparation or may be added in one, two or more step(s). Here an effective amount is to refer to an amount of phospholipase that is sufficient to cause a measurable effect on at least one property of interest of the dough and/or the bakery product.

The expression "improved property" is defined herein as any property of the dough and/or the product that is obtained from the dough, particularly a bakery product, that was improved by the effect of the phospholipase based on the dough or the product to which the phospholipase according to the invention was not added. The improved property may comprise, for example: improved strength of the dough, improved elasticity of the dough, improved stability of the dough, reduced stickiness of the dough, improved extensibility of the dough, improved machine runability of the dough, improved volume of the bakery product, improved crumb structure of the bakery product, improved softness of the bakery product, improved aroma of the bakery product and/or delayed staling of the bakery product. Processes to determine these properties are well known in the state of the art.

A dough is herein defined as a mixture of flour and other ingredients, which is as solid as to be kneaded or rolled. The dough may be fresh, frozen, pre-cooked or pre-baked.

The expression "bakery product" refers herein to any product that is prepared by a dough and has either a soft or a crisp character. Examples of bakery products that may be prepared by means of a phospholipase according to the invention are, for example, bread (particularly white bread, wholewheat bread or rye bread), typically in the form of loaves or French bread of the type French baguettes, pasta, pita bread, tortillas, tacos, cakes, pancakes, cookies or pastries, cooked bread, double-baked bread and the like.

In the preparation of these bakery products the polypeptide with phosopholipase activity according to the invention and/or one or more further enzyme(s) in any formulation that is suitable for the respective use may be added, for example, in a dry form, as liquid or as premix. Furthermore, one or more further enzyme(s) may be added to the dough. These further enzymes may be of any origin and may derive from mammals or plants, for example. Preferably, they are of a microbial origin and are particularly preferably derived from bacteria or fungi.

According to a preferred embodiment, the further enzymes may be amylases such as $\alpha$-amylase (suitable for producing sugars that are fermentable by yeasts and for delaying staling) or $\beta$-amylase, cylcodextrin glucanotransferase, peptidase, particularly an exopeptidase (suitable to increase the aroma), transglutaminase, lipase (useful for modification of the lipids present in the dough or parts of the dough to make the dough softer), phospholipases (useful for modification of the lipids that are present in the dough or parts of the dough to make the dough softer and to improve the gas retention in the dough), cellulase, hemicellulase, particularly a pentosanase such as xylanase (useful for the partial hydrolysis of pentosanes improving the extensibility of the dough), proteases (useful for the gluten softening, particularly if durum flour is used), protein disulphide disomerase (for example, a protein disulphide isomerase disclosed in WO 95/00636), glycosyl transferase, peroxidase (useful to improve the consistency of the dough), laccase or oxidase, for example, an aldose oxidase, glucose oxidase, pyrano oxidase, lipoxy-genase or L-amino acid oxidase (useful to improve the consistency of the dough).

This/These optionally further added enzyme/enzymes may be optionally added separately or together with the polypeptide with phospholipase activity according to the invention as components of baking agents or dough additives. The invention also relates to the preparation of such doughs as well as the preparation of corresponding bakery products made of these doughs.

The invention also relates to a premix, for example, in the form of a flour composition, for the preparation of dough and/or bakery products made of dough, whereby this premix comprises polypeptides with phospholipase activity according to the invention.

The polypeptides with phospholipase activity according to the invention may also be used as additive to animal feed. Adding phospholipases to feed improves the efficiency of feed uptake of animals. The growth of animals that are nourished with such feed is thereby improved. A phospholipase according to the invention may hereby be added as such or as feed concentrate. Furthermore, the phospholipase may also be added to the animal feed via transgenic plants, whereby the phospholipase is synthesized by heterologous gene expression. Processes for the production of such transgenic plants are disclosed in WO 91/14772.

The polypeptides with phospholipase activity according to the invention may also be used in the process of scouring in the processing of textile raw materials of, e.g., cotton fibres, to facilitate the further treatment of the fibres. The improvements obtained by scouring also have effects on the behavior during staining as well as the further mechanic and enzymatic processing of the fibres and the fabric made thereof.

The gene for the phospholipase that was isolated from the micro-organism *Aspergillus fumigatus* was deposited in the plasmid B11B1Hind6 under accession number DSM 18369 at the Deutschen Sammiung von Mirkorganismen und Zellkulturen GmbH (DSMZ), Mascheroder Weg 1b, D-38124 Braunschweig on 06/14/2006 in accordance with the provisions of the Budapest Treaty.

BRIEF DESCRIPTION OF THE DRAWINGS

The invention is further described on the basis of the enclosed figures. It is shown in:

FIG. 5: Nucleotide sequence and amino acid sequence derived therefrom of the chromosomal phospholipase gene from *Aspergillus fumigatus* RH3949. The introns are printed in italics. The matching of the amino acid sequence with the peptide sequences detected in the protein sequencing is underscored (cf. SEQ ID NOs: 1 and 2).

FIG. 6: The nucleotide sequence of the chromosomal phospholipase gene from *Aspergillus fumigatus* RH3949 (SEQ ID NO: 1).

FIG. 7: The amino acid sequence of the phospholipase gene from *Aspergillus fumigatus* RH3949 (SEQ ID NO: 2).

DETAILED DESCRIPTION OF THE INVENTION

Figure 1:
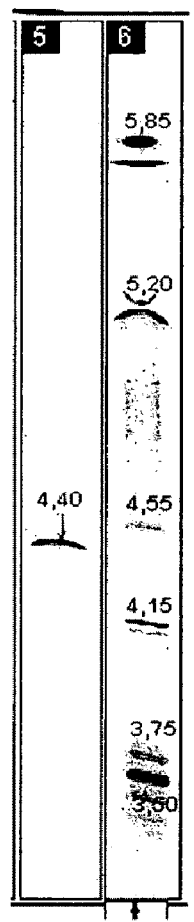
FIG. 1: IEF gel of purified phospholipase from *Aspegillus fumigatus*. The right track (no. 6) contains the marker proteins from the Isoelectric Focusing Calibration Kit, pH 2.5-6.5, company Pharmacia, no. 17-0472-01. The phospholipase band on the left track (no. 5) at pi 4.4 is identified by a narrow.

The following examples will specify the invention in detail:

REFERENCE EXAMPLE 1

Determination of the Phospholipase Activity 1 phospholipase unit corresponds to the amount of enzyme that releases 1 μmol fatty acid per minute from the phosphatidyl choline under standard conditions.
Reagents:
Substrate Solution:

1 g Epikuron 200 (purified phosphatidyl choline from soy by LUCAS MEYER, reference number 139029), 100 ml deionized water and 5 ml 0.32 M $CaCl_2$ solution are homogenized by means of an Ultra Turrax for 2 min at 24,000 rpm. The substrate solution is stable at 4°-8° C. for 3-4 d.
Other Solutions:

0.32 M CaCl.sub.2 solution, fresh 3.3 mM citric acid—monohydrate solution, 10 mM KOH solution, 1% TRITON X100 (company Fluka) solution in demineralized water.

Enzyme Solution

The enzyme preparations are solved in deionized water. The enzyme concentration in the batch may not exceed 2.5 U $g^{-1}$.

Carrying Out the Determination
Main Values 10 ml substrate solution
10 ml 1% Triton X100 solution
5 ml 3.3 mM citric acid—monohydrate solution are pipetted in a 25 ml wide-necked Erlenmeyer flask and tempered at 40° C. for 10 min. The pH value adjusts to 3.3-3.5.

After adding 0.1 ml of enzyme solution, the analysis batch is incubated at 40° C. for 10 min. When the incubation time is over, it is titrated to pH 10.0 with 0.01 M KOH, whereby the first 5 ml of KOH are added rapidly (duration: about 1 min). The consumption of KOH is registered.
Blank Test The enzyme parent solution is heated at 95° C. for 15 min and, thus, deactivated. After cooling down to room temperature, the further treatment is the same as for the main values.

An incubation of the bland samples is not necessary.
Evaluation:

$$PLU/g = \frac{\Delta V_{KOH} * c_{KOH} * 1000}{\Delta t * c_s * v}$$

| | | |
|---|---|---|
| $V_{KOH}$ | [ml] | difference in consumption between the blank value and the main value |
| $c_{KOH}$ | [mol l$^{-1}$] | concentration of KOH |
| t | [min] | incubation time |
| $c_s$ | [g ml$^{-1}$] | concentration of the sample |
| v | [ml] | volume used |

EXAMPLE 1

Preparation of Phospholipase with *Aspergillus fumigatus*

*Aspergillus fumigatus* RH3949 IS15 was grown in 200 ml shaking flasks filled with 50 ml medium at 28° C., 200 rpm, over 5 d. The medium consisted of 0.5% Epicuron 200 (Lucas Meyer), 0.5% corn steep powder, 0.2% $NH_4NO_3$, 100 mM $KH_2PO_4$ and 0.1% Triton X100. The pH value was adjusted to pH 6 before sterilisation. The medium was inoculated with a spore suspension. After 5 days, the culture supernatant was separated from the mycelium by filtration, and the phospholipase activity in the liquid was measured.

EXAMPLE 2

Purification of the Phospholipase from *Aspergillus fumigatus*
Step 1: Anion Exchanger Concentrated culture supernatant from the cultures of Example 1 was separated into protein fractions by means of an anion exchanger.

The sample was dialyzed against completely desalinated water in a dialyse tube (Naturin protein farce) for 1.5 h. The pH value was adjusted to pH 7 with 1 M NaOH. The phospholipase with the pI of about 4.4 is not adsorbed on the column Macro Prep Q (company BioRad 156-0051) if this column is equilibrated with 20 mM Tris/HCl buffer pH 7+5 mM $CaCl_2$ but retrieved in the through-flow.
Step 2: HIC (Hydrophobic Interaction Chromatography)

The through-flow of the first step was adjusted to an ammonium sulphate concentration of 1.7 M by concentrated ammonium sulphate solution. The sample solution was applied to the HIC column, Phenyl Separose 6 Fast Flow low substitution (company Pharmacia 17-0965-03) with an ammonium sulphate concentration of 1.7 M.

The phospholipase was found in the flow of the column equilibrated with 20 mM Tris/HCl buffer pH 7+5 mM $CaCl_2$+ 1.7 M ammonium sulphate.

Step 3: Chromatic Focussing

The flow according to step 2 was newly buffered with the Jumbosep centrifugal concentrator and 10 kDa membrane insert (company Pall Filtron, no. FD 010K65) with eluent A (0.025 M histidine/HCl pH 6.2) and concentrated.

Now the sample was loaded on the MONO P, MONO P HR 5/20 (company Pharmacia 17-0548-01), which is equilibrated for a pH range of pH 6-4 [eluent B polybuffer 74, company Pharmacia 17-0713-01), pH 4].

The phospholipase was retrisved in the elute.

The partially purified phospholipase was applied to an IEF gel (FIG. 1). The bands were cut out for identification and examined for phospholipase activity according to the described methods of analysis.

Figure 2:
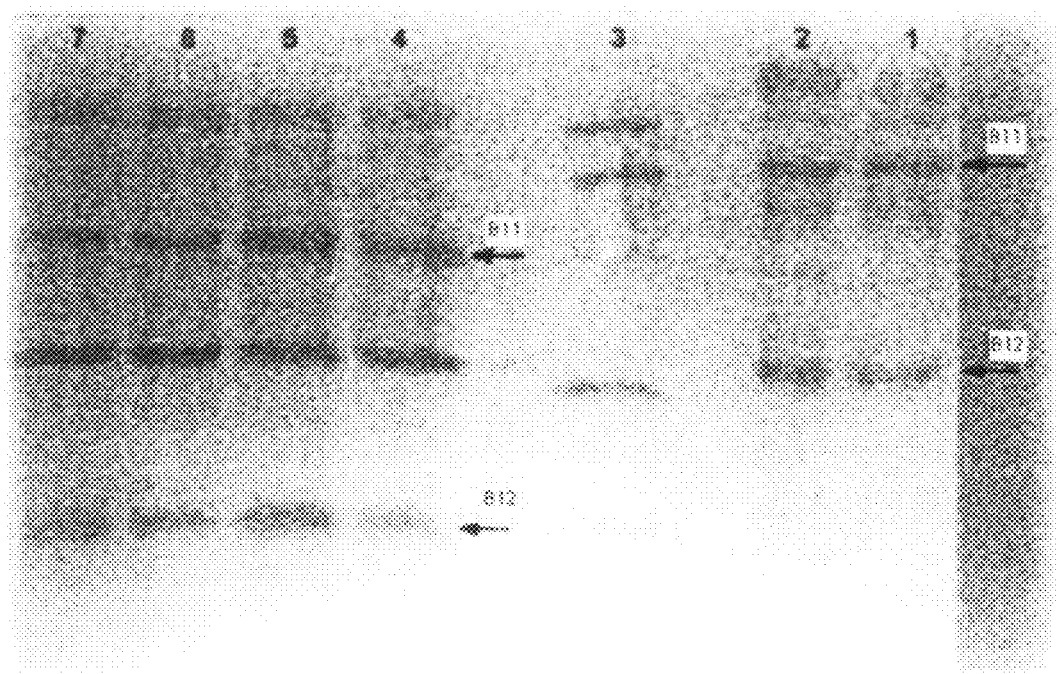
FIG. 2: SDS gel of the partially purified phospholipase from *Aspergillus fumigatus* before (track 1 and 2) and after treatment with N-gycosidase F (tracks 4, 5, 6 and 7). Track 3 contains the marker proteins (SDS-PAGE standards, low range: 97,400, 66,200, 45,000, 31,000, 21,500, 14,400, Bio-rad).

Subsequently, the phospholipase bands were applied to a SDS gel not only directly but also after deglycosylation with N-GLYCOSIDASE F (New England BioLabs Inc.). 2 bands with about 72 and 34 kDa or after deglycosylation with about 54 and 20 kDa (FIG. 2), which were further used in Example 4, were recovered.

EXAMPLE 3

Characterization of the Phospholipases from *Aspergillus fumigatus*

Figure 3:
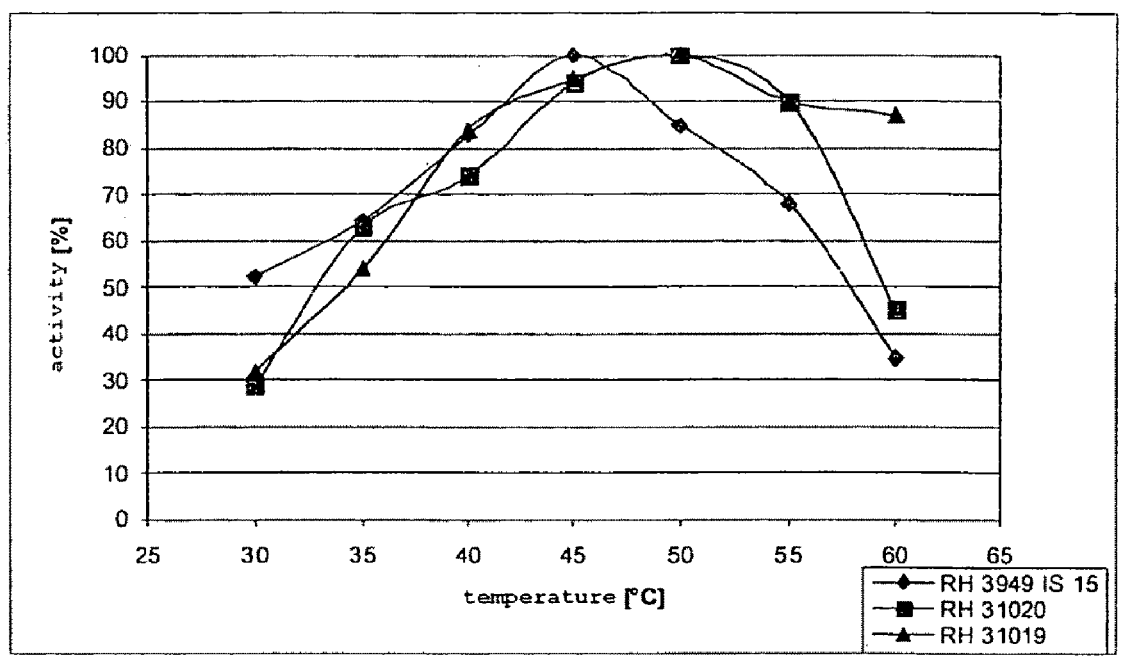
FIG. 3: T optima curve for the phospholipase from *Aspergillus fumigatus* (RH 3949 IS15) culture supernatant and recombinantly expressed in *Aspergillus niger* (RH 31019 and RH 31020).

The phospholipase activity was detected by the method of determination as described above at different temperatures. The curve in FIG. 3 shows a T-optimum at a temperature of 45° C. for the enzyme produced natively by means of *Aspergillus fumigatus* RH 3949 IS15 (cf. Example 1) as well as a T-optimum of 50°-52° C. for the enzyme produced recombinantly by means of *Aspergillus niger* strains (cf. Example 5). The residual activity at 60° C. was increased from 35% to 87% in the enzyme produced recombinantly.

Figure 4:
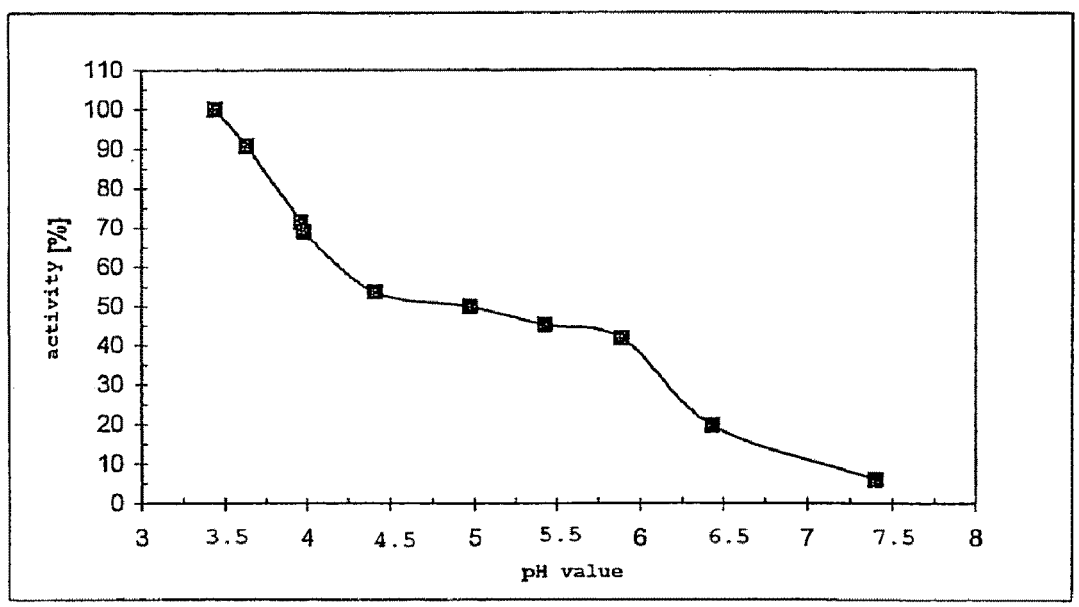
FIG. 4: pH optima curve for phospholipase from *Aspergillus fumigatus* RH3949 IS15).

The phospholipase activity was detected as described above at different pH values. The pH value was thereto adjusted by means of citric acid. The curve in FIG. 4 shows a pH optimum at values of pH 3.5 and lower as well as a second local pH optimum at pH 5-6 and, thus, optimal properties for the application in oil degumming at pH values of <5 to prevent deposition of Ca compounds in the centrifuge.

EXAMPLE 4

Isolation and Determination of the DNA Sequences of the Phospholipases from *Aspergillus fumigatus* a) N-Terminal Protein Sequencing

After the final purification step via Mono P (chromatic focusing), the fractions with the highest phospholipase activity were collected and separated on a native gel. The protein band with phospholipase activity was cut out and applied on a SDS gel again. Two fragments, referred to as B11 and B12, with a molecular weight of about 72 kDa or 34 kDa were thereby found. After deglycosylation with N-glycosidase F (New England BioLabs Inc.) they had molecular weights of about 54 and 20 kDa. The protein bands marked in FIG. 2 as B11 and B12 were transferred to a PVDF membrane (Fluotrans Transfer Membrane, Pall) and the N-terminal amino acid sequences were determined in an amino acid sequencer (Applied Biosystems Model 470A) after Comassie staining. They are:

```
B11: DSASY⁵ YKDYS¹⁰ NAVSG KAD¹⁸     (SEQ ID NO: 3)

B12: ALPNA⁵ PDGYT¹⁰ PS-VG-PA¹⁸     SEQ ID NO: 4)
```

It is remarkable that the fragments B11 and B12 do not show matchings with the sequences of known phospholipases. They are similar to the sequences of lysophospholipases. It was all the more surprising that a phospholipase was found due to fragments B11 and B12.

b) Determination of the Amino Acid Sequence of BRCN Fragments

The BrCN cleavage of proteins was carried out according to a specification by Gross (1967, The Cyanogen Bromide Reaction, Methods Enzymol, vol. XI, 238-255). Here protein fragments B11 and B12 were cut out of the gel after SDS gel electrophoresis, washed with 40% n-propanol and subsequently incubated in a mixture of 750 mM BrCN in 70% formic acid at room temperature for 24 h in the dark. The protein fragments in the supernatant were taken up in buffer after eliminating the bromocyanogen in the vacuum centrifuge and then applied to a SDS gel according to Schagger and Jagow (1987, Anal. Biochem. 199, 223-231) for separation of small protein fragments.

After the gel electrophoresis, the fragments from the gel were transferred to a PVDF membrane (polyvinylidene difluoride membranes), which were identified by the Coomassie staining and used for protein sequencing (Matsudaira, 1987, J. Biol. Chem. 262, 10035-10038).

The amino acid sequences of the following BrCN fragments from protein B11 or B12 were determined:

```
B11/1  ¹DSASY                       (SEQ ID NO: 5)

B11/2  ¹PVVVA DGNYP¹⁰               (SEQ ID NO: 6)

B11/5  ¹-TSST LFNQF¹⁰               (SEQ ID NO: 7)

B12/1  ¹KDFFS HVKIQ¹⁰ DFDAV GYID¹⁹  (SEQ ID NO: 8)

B12/2  ¹ALPNA                       (SEQ ID NO: 9)

B12/3  ¹NTATA IKAFD¹⁰ S-TP¹⁴        (SEQ ID NO: 10)
``` c) Synthesis of the 1-cDNA Strand

About 1×10⁷ spores of the *A. fumigatus* strain RH 3949 IS15 were inoculated into 100 ml medium (0.5% corn steep powder, 0.5% Epikuron 200, 0.1% Triton X100, 0.2% $NH_4NO_3$ and 100 mM $KH_2PO_4$ pH 6.0) and cultivated at 45° C. for 2 to 3 day The obtained mycelium was used for RNA preparation by means of the Qiagen column (Qiagen).

The synthesis of the 1-cDNA strand was carried out according to the specifications of the manufacturer (BRL). 4 µl 5× BRL buffer (250 mM Tris/HCl, pH 8.3, 375 mM KCl, 15 mM $MgCl_2$), 1 µl 10 mM dNTP, 2 µl 100 mM DTT, 50 pmol primer EA13, 1 µl RNA (2 µg total RNA) and 2,000 U RTASE SUPER SCRIPT (BRL) were pipetted together in a 20 µl reaction batch. The reaction batch was incubated at 45° C. for 50 min.

For the later amplification of the phospholipase cDNA by means of the polymerase chain reaction, the batch was diluted with 20 µl distilled water and stored at −0° C.

The DNA sequence of the primer EA13 is:

```
                                           (SEQ ID NO: 11)
5'-gAC TCg AgT CgA CAT CgA (T)₂₀ (A/C/g)-3'
``` d) Amplification of a Partial Sequence of Phospholipase cDNA by Means of the Polymerase Chain Reaction (PCR)

Different oligoprimers for the amplification of the phospholipase cDNA were derived from the above data of the amino acid sequence. The PCR products were cloned in the PGEMT plasmid and sequenced. Compared to the sequencing data of Example 4b), it was found that the primer couple B12/B5 and B12/B8 leads to the correct phospholipase cDNA gene fragment.

```
B12/B5 Primer
                                           (SEQ ID NO: 12)
5'-gAC TTT gAC gCT gTg ggg TAC ATC gA-3'

B12/B8 Primer
                                           (SEQ ID NO: 13)
3'-TAC TTg TgA CgA Tgg CgT TAg TTC CgA AAA CT-5'
```

The amplification of a partial sequence of phospholipase cDNA was carried out with the batch of the first cDNA synthesis by means of the PCR method. The reaction batch of 100 μl comprised: 10 μl 10× buffer (200 mM Tris/HCl, pH 8.4, 500 mM KCl), 2 μl 10 mM dNTP, each 50 pmol oligoprimer (B12/B5 and B12/B8), 1 μl of the batch of the 1st strand cDNA, 5 U Taq DNA polymerase (BRL). The batch was treated for denaturation at 95° C. for 5 min, 45 cycles (95° C for 1 min each, 45° C for 1 min, 72° C. for 1 min) and subsequently the extension was carried out at 72° C. for 5 min.

The PCR products were purified on a Qiaquick column and cloned in pGEMT plasmid.

One transformant comprised the correct partial sequence of phosopholipase cDNA after sequencing and was referred to as B12/14/1.

e) Cloning of the Chromosomal Phospholipase Gene from the Strain RH3949 IS15

The chromosomal DNA preparation was carried out according to a specification by Hynes, M. J et al. (1983) Mol. Cell. Biol. 3, 1430-1439.

After the Sau3A I partial hydrolysis, the DNA was fractioned according to size by means of a saccharose density gradient centrifugation. Fractions that contained DNA fragments of 9-20 kb were combined and precipitated with ethanol at –0° C. After washing and drying, the DNA was inserted in EMBL3 DNA hydrolyzed by BamHI/EcoRI and packaged in vitro. Packaging in the phage lysate Gigapack II Gold Packaging was carried out according to the specification described by the manufacturer (Stratagene Instruction Manual).

To identify the chromosomal phospholipase gene in a lambda EMBL3 gene bank, the cDNA fragment from the plasmid B12/14/1 was used as radioactive gene probe. The hybridization was carried out at 65° C. for 18 h in dextran sulphate solution (GenescrenePlus, DuPont). After hybridization, the filters were washed each for 30 min, first with 6×SSC, twice 2×SSC, twice 2×SSC, 0.1% SDS and subsequently with 0.2×SSC at 65° C. (membrane transfer and detection methods, Amersham).

Eight positive clones were identified. From the results of the analysis with the restriction endonucleases and southern hybridization with the gene probe isolated from B12/14/1, the phage DNA of the clone B1 was hydrolyzed with HindIII.

Figure 8:
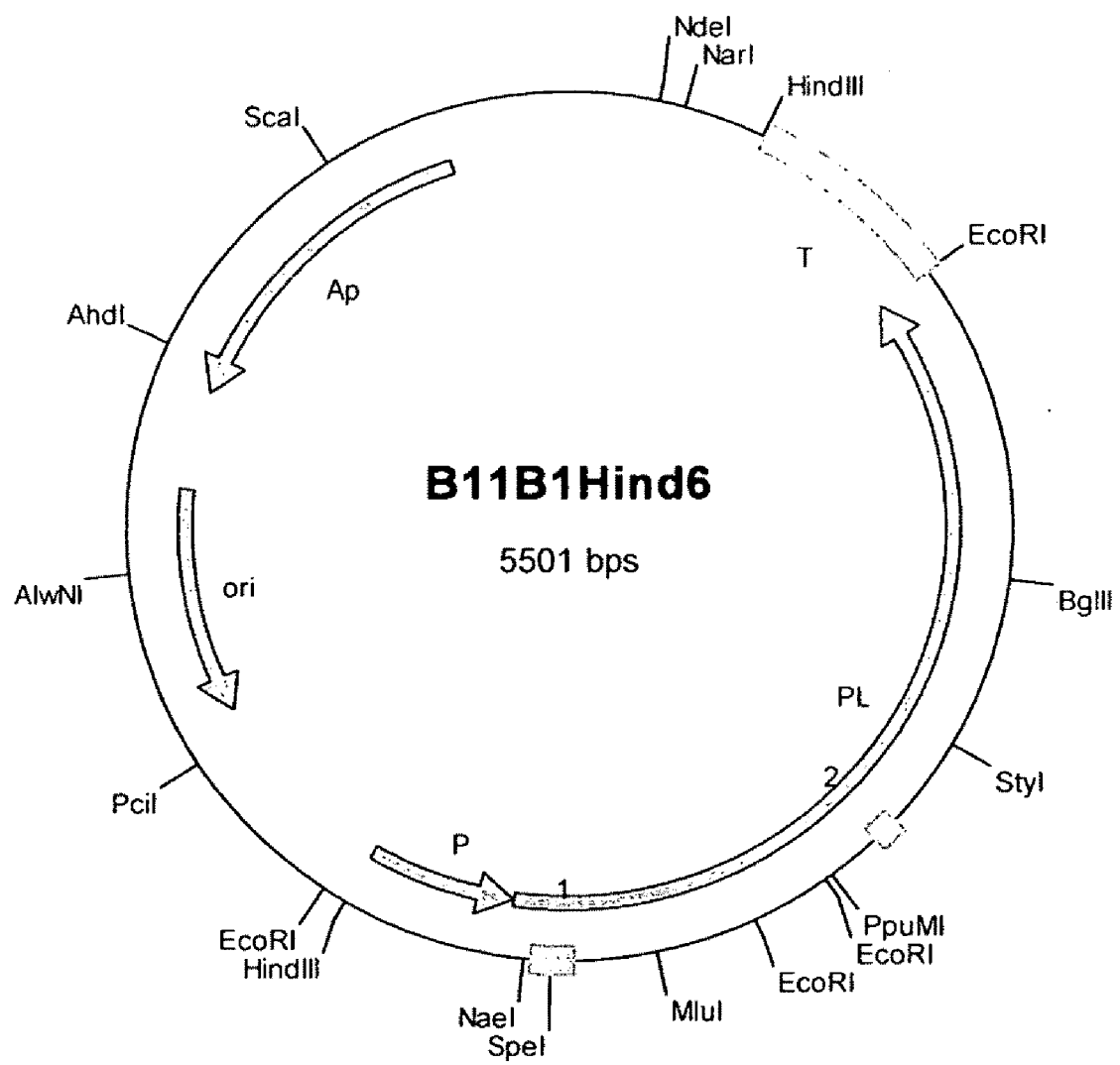
FIG. 8: Restriction map of the vector B11B1Hind6

The 2.8 kb HindIII fragment inserted in pUC18 was referred to as B11B1Hind6 (FIG. 8) and the nucleotide sequence of the 2.8 kb DNA fragment was determined by sequencing.

f) Cloning and Characterization of the N-Terminal Region of the Phospholipase cDNA To determine the position of the initiation codon or the signal sequence of the phospholipase gene, the amplification of the N-terminal region of the phospholipase cDNA was carried out by PCR.

The oligoprimer B12A2P5 or B12A2P9 used for this was derived from the data of the chromosomal DNA sequence and synthesized.

```
B12A2P5
5'-CTT TGC GGC ACT GCG AAT-3'    (SEQ ID NO: 14)

B12A2P9
5'-ATA TTT GAT CTT ATT GTC-3'    (SEQ ID NO: 15)
```

The PCR was carried out under the same conditions as in Example 4e). The obtained PCR product was cloned in pGEMT vector (Promega) and sequenced.

By comparing the cDNA sequence with the chromosomal sequence, the presence and the location of the phospholipase ATG start codon was determined. The determination of the signal sequence was carried out by a computer program (PSORT) of Nakai and Kanehisa (1992, Genomics 14, 897-911). Thereupon the phospholipase gene has a signal sequence of 20 amino acids, a potential propeptide of 12 amino acids and the intron 1 with 87 bases.

g) Cloning of the C-Terminal Region of the Phospholipase cDNA in the same process as in Example 4f), the C-terminal region of the phospholipase cDNA was amplified. The oligoprimers used for this have the following sequence:

```
B11B1P15
                                           (SEQ ID NO: 16)
5'-GGC GCA GGT GCG ATT AAG GCT TTT GA-3'

B11B1P13
                                           (SEQ ID NO: 17)
5'-TTC GCG AAA CTC TCG AAA TGA ATT CTA-3'
```

The obtained PCR product was cloned in the pGEMT vector, sequenced and referred to as cDNA 4/20. By comparing the phospholipase cDNA sequence and the chromosomal DNA sequence, the location of intron 2 with 56 bases in the phospholipase gene was confirmed.

h) Construction of the Expression Vector pK3949/9

In the expression vector pK3949/9 (FIG. 9) the phospholipase gene without intron 2 is under control of the A. oryzae α amylase promoter.

The expression vector pK3949/9 was constructed in three steps:

Introduction of a BspHI cleavage site at the start codon by means of the PCR method.

The primers used for this have the following sequence:

```
Primer B11B1N3
                                           (SEQ ID NO: 18)
5'-CGC GGA TCC GTC ATG AAG TCC ATC GCA GTG GCG
TGC -3'

Primer B11/B11
                                           (SEQ ID NO: 19)
5'-TTG ACT AGT TTG AAC CAC ACT TCA AG-3'
```

The PCR was carried out under the same conditions as in Example 4d). The PCR product was hydrolyzed by the enzymes BamHI/SpeI and subsequently inserted in the B11B1Hind6 hydrolyzed with the same enzymes. The obtained plasmid has the designation pK3949/1.

The phospholipase gene was built into the plasmid pK54 cut with NcoI/HindIII from the plasmid pK3949/1 as BspHI/HindIII fragment. The obtained plasmid pK3949/2 comprises the phospholipase gene under the control of the *A. oryzae* α-amylase promoter.

The plasmid pK54 comprises the promoter sequence of the *A. oryzae* α-amylase gene. The α-amylase promoter sequence was isolated from *A. oryzae* DSM63303 (Wirsel et al. 1989, Mol. Microbiol. 3 (1), 3-14), modified by PCR and comprises a NcoI cleavage site-immediately upstream of the ATG codon.

Figure 9:
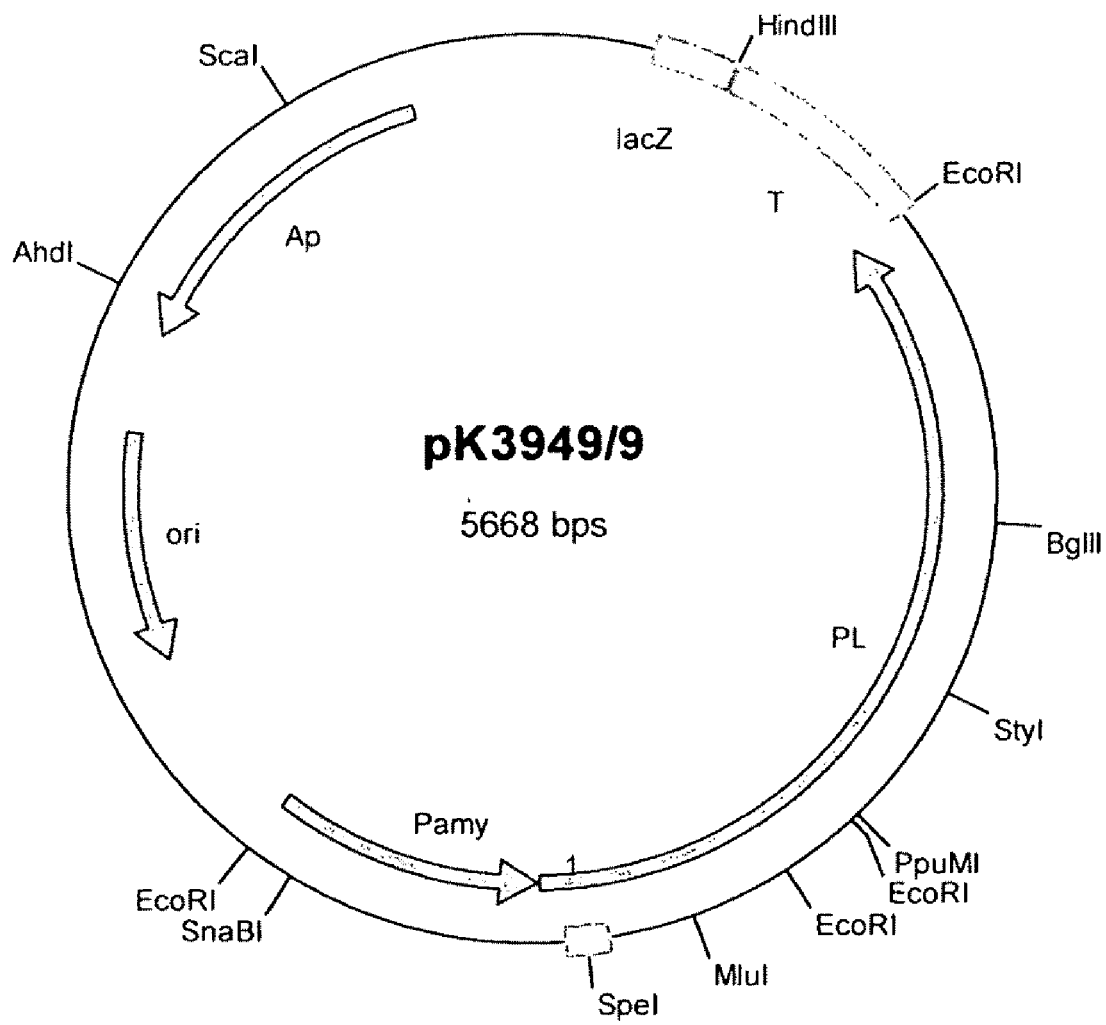
FIG. 9: Restriction map of the expression vector pK3949/9

By replacing the PpuMI/StyI fragment by the PpuMi/StyI fragment islated from the plasmid cDNA 4/20, the expression vector pK3949/9 was constructed (FIG. 9).

i) Construction of the Expression Vector pK3949/11

Intron 1 and the propeptid were deleted in the vector pK3949/11 (FIG. 10), so that the phospholipase gene with own signal sequence directly fuses at the *A. oryzae* α-amylase promoter. The vector pK3949/2 was used as starting plasmid. The isolation of individual fragments was carried out by the PCR method, whereby the reaction conditions were kept according to Example 6d). The following primers were used:

```
                                    (SEQ ID NO: 20)
K17 5'-GAA TTC TGG TGT TTT GAT CTT TT-3'

(SEQ ID NO: 21)
K18 5'-AGC ACC GCT AGC ACC GGA CAA TAA TAG GCC GGC
    GAC-3'

(SEQ ID NO: 22)
K19 5'-TCC GGT GCT AGC_GGT GCT GCC CTG CCC AAT GCC
    CCC GAT GGA TAC ACA-3'

(SEQ ID NO: 23)
K20 5'-GAA GTC CTT CAT CGC AGA AGT-3'

(SEQ ID NO: 24)
K21 5'-CTG ATA TTT ACG TAA AAA TCG TCA-3'

(SEQ ID NO: 25)
K22 5'-CTT GCC TCG ACG CGT CTG AAG CCA TGA-3'
```

Figure 10:
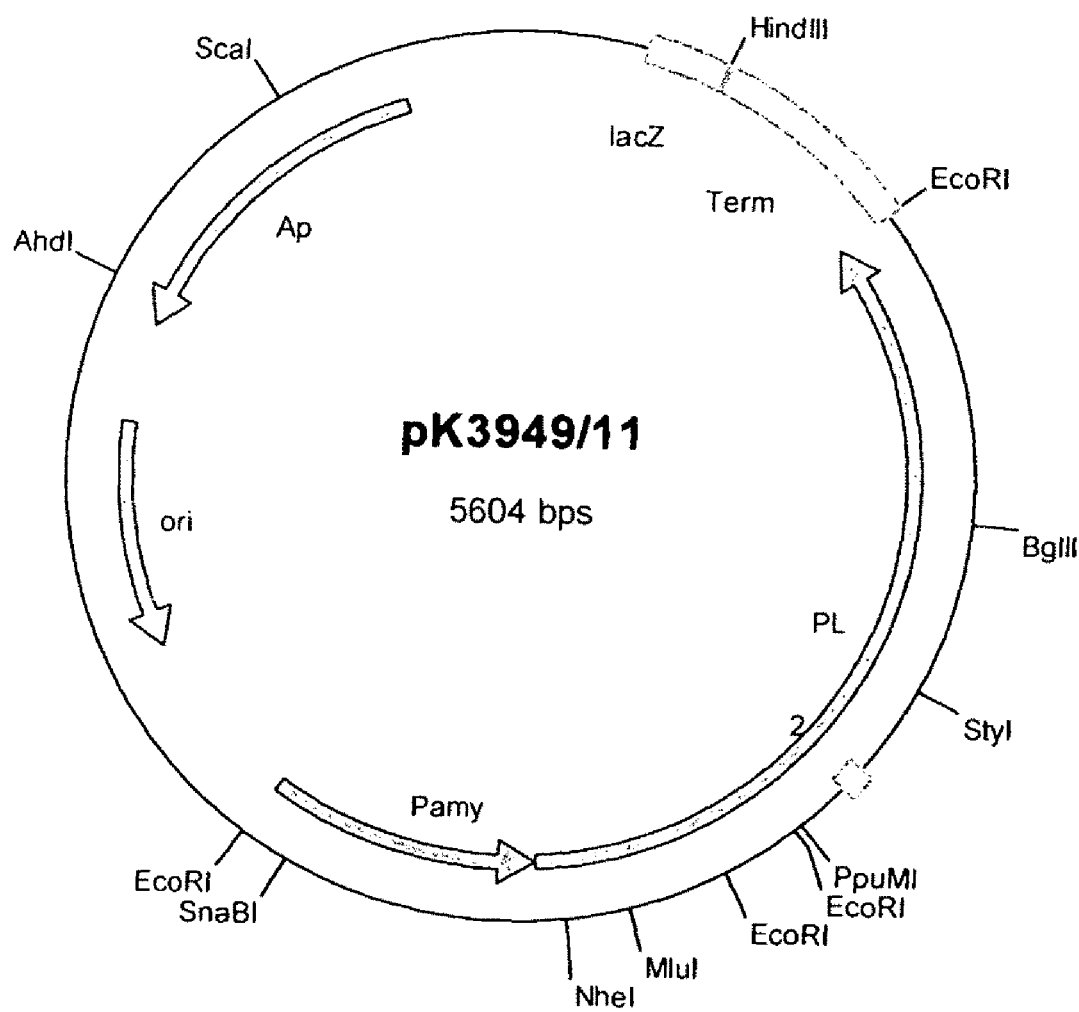
FIG. 10: Restriction map of the expression vector pK3949/11

The gene sections consisting of the *A. oryzae* α-amylase promoter and the phospholipase signal sequence were amplified by the primer pairs K17/18. The gene sections consisting of the phospholipase signal sequence and the N-terminal part of the phospholipase gene were amplified by the primer pairs K19/K20. By replacing the bases, the NheI cleavage site was introduced without alterations in the amino acid composition. The PCR products were purified, hydrolyzed with Nhel and ligated together. The ligation product serves as a matrix and the oligos K21 and K22 as primers for the second PCR batch. The obtained PCR fragment was hydrolyzed with SnaBI/MluI after purification and subsequently inserted into the plasmid pK3949/2 cut with the same enzymes. The obtained vector has the designation pK3949/11 (FIG. 10).

EXAMPLE 5

Transformation of *A. niger* NRRL3 with DNA from *Aspergillus fumigatus*

The isolation of protoplasts and the transformation of *A. niger* was carried out according to the method by Yelton et al. 1984, Proc. Natl. Acad. Sci. USA 81, 1470-1474.

The plasmid pAN7-1 (Punt et al., 1987, Gene 56, 117-124) was used as selection plasmid for the co-transformation of *A. niger*.

10 µg selection plasmid and 10 µg expression plasmid were presented together in 20 µl $H_2O$ in an Eppendorf vessel. 200 µl protoplast suspension (about $2 \times 10^7$ protoplasts) were added to the plasmid solution, carefully mixed by reversion, and subsequently incubated at room temperature for 5 min. After adding 50 µl PTC solution (60% polyethylene glycol 6000, 10 mM Tris/HCl pH 7.5, 50 mM $CaCl_2$), an incubation at room temperature for 20 min took place. After a further addition of 750 µl PTC solution and a further incubation at room temperature for 20 min, the batch was centrifuged in the Eppendorf centrifuge for 1 to 2 min. The protoplasts were carefully re-suspended in 1 ml STC solution (1.0 M sorbitol, 10 mM Tris/HCl pH 7.5, 50 mM $CaCl_2$) and plated on 10-15 selection agar plates (per liter: 33.4 Czapek-Dox-Liquid Medium (Oxoid), 1 M saccharose and 12 g highly pure Agar No. 1 (Oxoid) and 100 mg Hygromycin B (Sigma).

Then the plates were incubated at 30° C. for 5 to 7 d until sporulation. To obtain genetically pure clones, the transformants were singled out on selection agar plates twice. Three transformants, RH 31019, RH 31021 and RH 31025, were selected for further experiments.

EXAMPLE 6 (REFERENCE EXAMPLE)

Degumming of Oil

In a first step the phospolipide content was reduced to 120 ppm phosphorus by water degumming in canola oil with 535 ppm phosphorus content to further decrease the phospholipide content by enzyme addition in a subsequent second step. The water phase of the water degumming was not discarded but remained in the reaction batch. A separation may also be possible.

250 g canola oil were filled into a three-necked round-bottomed flask and moved in circle by turning on the rotary pump (Metabo header pump 27621) until the oil reached the reaction temperature of 60° C. Then the citric acid was added to the oil at a final concentration of 0.1% (w/v). After 120 min, the pH value was adjusted to pH 4.0 by adding 7% NaOH solution to provide optimal working conditions for the enzyme. When the reaction temperature of 60° C. to 65° C. was reached, the enzyme solution was added resulting in enzyme activities of 250 to 3,000 PLU per kg raw oil. The total water content of all aqueous dosages (citric acid, NaOH, enzyme solution) is 1% to 5% in the oil. The reaction batch was well mixed during the additions. The flask was always securely closed to avoid evaporation of the water. A sample of 20 ml was taken each 120 min after addition of the enzyme solution. The samples were centrifuged at 4,300×g for 5 min and the phospholipide content, shown in ppm phosphorus, was photometrically determined as phosphorus molybdate complex at 830 nm in the oil after ashing at 850° C. by adding magnesium oxide.

The phospolipide content may also be flame-photometrically determined directly in the oil by means of an AAS device.

EXAMPLE 7

Results with Enzyme from Culture Supernatants of *A. fumigatus* RH 3949 IS15

Culture supernatants of RH 3949 IS15 of Example 1 were used at different temperatures (62.5°-65° C.) to degum canola oil according to Example 6. All experiments were carried out at pH 4 and a total water content of 5%.

TABLE 1

Degumming of Canola Oil (605 ppm P) With Phospholipase
Enzyme from Culture Supernatants of *Aspergillus fumigatus*
RH3949 IS15 and 5% Water Content at pH 4.0

| sample designation | time [min] | 62.5° C. [ppm P] | 64° C. [ppm P] | 65° C. [ppm P] |
|---|---|---|---|---|
| citric acid | 90 | 115.4 | 115.4 | 115.5 |
| | 180 | 106.0 | 106.0 | 101.1 |
| | 270 | 85.7 | 85.7 | 87.0 |
| | 360 | 79.2 | 79.2 | 73.7 |
| 500 PLU kg$^{-1}$ raw oil | 90 | 76.1 | 80.0 | 97.7 |
| | 180 | 18.0 | 51.3 | 80.4 |
| | 270 | 12.6 | 35.1 | 64.6 |
| | 360 | 10.4 | 30.0 | 53.7 |
| 1000 PLU kg$^{-1}$ raw oil | 90 | 35.2 | 27.3 | 60.7 |
| | 180 | 13.3 | 10.8 | 31.6 |
| | 270 | 10.0 | 8.8 | 23.3 |
| | 360 | 7.2 | 9.5 | 20.0 |

The results show a clear degumming effect by the enzyme compared to the water degumming of citric acid. The effect also depends on the dosage (comparison of 500 PLU kg$^{-1}$ with 1,000 PLU kg$^{A1}$) and the enzyme may be used at temperatures up to 65° C. Therefore, the heat stability of the enzyme in oil degumming is clearly higher than in the determination in aqueous solution as carried out in Example 3.

By the separation of the water phase and the mud phase described in Example 6, the enzyme-containing fraction may be recovered and may be added again to an attempt to degum oil. The following table depicts the results of up to five repetitions.

TABLE 2

Degumming of Canola Oil (605 ppm P) with Phospholipase Enzyme
from Culture Supernatants of *Aspergillus fumigatus* (RH3949
IS15 and 5% Water Content at pH 4.0, 60° C. and 1,000
PLU per kg Raw Oil Added to the First Cycle.

| cycle | [ppm P] after 6 h |
|---|---|
| 1 | 5.4 |
| 2 | 6.0 |
| 3 | 6.3 |
| 4 | 13.6 |
| 5 | 27.4 |

In Any Further Cycle Only the Aqueous Phase (Water and Mud) Was Used After Centrifugation of the Preceding Cycle.

The results show that the enzyme may be used more than three times (i.e., >18 h) without any significant inactivation.

EXAMPLE 8

Results with Enzyme from Culture Supernatants of Recombinant *Aspergillus niger* Strains with the Gene of *A. fumigatus* RH 3949 IS15

The recombinant *A. niger* NRRL3 strains of Example 5, which comprise the plasmids B11B1Hind6, pK3949/9 and pK3949/11, have the designations RH31019, RH31021 and RH31025. The degumming results of canola oil with these strains are listed in Table 3. It is shown there that the enzyme recombinantly prepared with *Aspergillus niger* RH31025 also has the heat stability of the enzyme prepared with wild-type strain *Aspergillus fumigatus* RH3949 IS15.

TABLE 3

Degumming of Canola Oil (535 ppm P) with Phospholipase
Enzyme (1,000 PLU per kg Raw Oil) from Culture Supernatants
of Recombinant *A. niger* Strains with 5% Water Content
at pH 4.0 (Not Determined)

| sample designation | time [min] | 60° C. [ppm P] | 64° C. [ppm P] |
|---|---|---|---|
| citric acid | 90 | 84.6 | 67.9 |
| | 180 | 72.7 | 47.2 |
| | 270 | 53.0 | 41.3 |
| | 360 | 49.7 | 38.5 |
| RH31019 | 90 | 53.2 | n.d. |
| | 180 | 30.7 | n.d. |
| | 270 | 18.5 | n.d. |
| | 360 | 8.8 | n.d. |
| RH31021 | 90 | 63.3 | n.d. |
| | 180 | 39.6 | n.d. |
| | 270 | 34.5 | n.d. |
| | 360 | 16.0 | n.d. |
| RH31025 | 90 | 49.3 | 26.8 |
| | 180 | 25.7 | 13.9 |
| | 270 | 16.7 | 6.8 |
| | 360 | 11.9 | 4.8 |

---

The invention claimed is:

1. An isolated DNA that encodes a polypeptide with phospholipase activity comprising:
   (a) a DNA that comprises the nucleic acid sequence of SEQ ID NO:1;
   (b) a DNA that encodes a protein, wherein said protein has the amino acid sequence of SEQ ID NO:2; and
   (c) a full complement of the DNA of (a) and (b).

2. The isolated DNA of claim 1, wherein the sequence is obtained from *Aspergillus*.

3. The isolated DNA of claim 2, wherein the sequence is obtained from *Aspergillus fumigatus*.

4. An isolated nucleic acid sequence that encodes a polypeptide with phospholipase activity, wherein said polypeptide has an amino acid sequence that is at least 92% identical to SEQ ID NO:2.

5. An expression construct that comprises the isolated DNA of claim 1.

6. The expression construct of claim 5, further comprising a promoter selected from the group consisting of glucoamylase promoter or α-amylase promoter of the genus *Aspergillus*, cellulose (cellobiohydrolase) promoter of the genus *Trichoderma*, phosphoglycerate kinase or glycerol aldehyde-3-phosphate dehydrogenase promoter, xylanase promoter and enolase promoter.

7. The expression construct of claim 5, further comprising a secretory leader sequence.

8. A recombinant host cell transformed with the expression construct of claim 5.

9. The recombinant host cell of claim 8, obtained from a fungus cell of the genus *Aspergillus Rhizopus, Trichoderma, Neurospora, Mucor* or *Penicillium*; or a yeast cell of the genus *Kluyveromyces, Saccharomyces, Schizosaccharomyces, Trichosporon, Schwanniomyces, Hansenula* or *Pichia*.

10. A process for the production of a polypeptide with phospholipase activity comprising the host cell of claim 8, culturing said host cell under conditions that support the expression of the polypeptide and recovering the polypeptide.

11. A full complement of the isolated nucleic acid sequence of claim 4.

* * * * *

SEQUENCE LISTING

<160> NUMBER OF SEQ ID NOS: 25

<210> SEQ ID NO 1
<211> LENGTH: 2822
<212> TYPE: DNA
<213> ORGANISM: Aspergillus fumigatus
<220> FEATURE:
<221> NAME/KEY: CDS
<222> LOCATION: (347)..(395)
<220> FEATURE:
<221> NAME/KEY: CDS
<222> LOCATION: (483)..(1140)
<220> FEATURE:
<221> NAME/KEY: CDS
<222> LOCATION: (1197)..(2388)

<400> SEQUENCE: 1
aagcttctcc accatcatat tcatgctttt cagcccttc agcaatgtgg tccgcggttc    60

```
aaactacgaa tgctccaatg gcaatcacct atctatcctt cgcgagggat gagaccaaat      120
cacattgttt caatctccca agactttggc atgcttggcc ttactgctga tccaccgtcc      180
caatatgaga accctggct aagggacacc gccccattta ttcaaatacc gaatgatggc       240
tgcctcacat tggggttggg tagagagagc gatatttgat cttattgtcc cctctagctg     300
aatcttcacg cggattatag cgtgaggtgg cctcatacga cccaag atg aag tcc        355
                                                   Met Lys Ser
                                                     1 atc gca gtg gcg tgc gct gtc gcc ggc cta tta ttg tcc g gtaggtgaat     405
Ile Ala Val Ala Cys Ala Val Ala Gly Leu Leu Leu Ser
  5              10                  15 cgttctgcct tgaagtgtgg ttcaaactag tcaaatccgc ctgcgaaact ggtactgatg     465
ccgtcggact tcaatag gt  gcg agt ggt gct cca gag ccc ttt cat ggt        514
                      Gly Ala Ser Gly Ala Pro Glu Pro Phe His Gly
                                   20                  25 gaa atc cta cag cgt gcc ctg ccc aat gcc ccc gat gga tac aca ccc       562
Glu Ile Leu Gln Arg Ala Leu Pro Asn Ala Pro Asp Gly Tyr Thr Pro
          30                  35                  40 agt aca gtc ggt tgt cct gcc agt cgc cct acc att cgc agt gcc gca       610
Ser Thr Val Gly Cys Pro Ala Ser Arg Pro Thr Ile Arg Ser Ala Ala
 45                  50                  55 aag ttg tcg ccc aac gag acg tca tgg ctt cag acg cgt cga ggc aag       658
Lys Leu Ser Pro Asn Glu Thr Ser Trp Leu Gln Thr Arg Arg Gly Lys
 60                  65                  70                  75 act act tct gcg atg aag gac ttc ttt agt cat gtc aag att caa gac       706
Thr Thr Ser Ala Met Lys Asp Phe Phe Ser His Val Lys Ile Gln Asp
              80                  85                  90 ttc gac gcg gtg ggg tac att gac cgc cat tcc agt aac tcg tcg gat       754
Phe Asp Ala Val Gly Tyr Ile Asp Arg His Ser Ser Asn Ser Ser Asp
              95                  100                 105 ctt ccc aat atc ggc atc gca atc tct ggt gga ggt tat cga gca ttg       802
Leu Pro Asn Ile Gly Ile Ala Ile Ser Gly Gly Gly Tyr Arg Ala Leu
              110                 115                 120 atg aac ggc gca ggt gcg att aag gct ttt gat agt cgt acg ccg aat       850
Met Asn Gly Ala Gly Ala Ile Lys Ala Phe Asp Ser Arg Thr Pro Asn
              125                 130                 135 tct acg agc ccc ggt cag ttg ggt gga ttg ctg cag tca gcc act tat       898
Ser Thr Ser Pro Gly Gln Leu Gly Gly Leu Leu Gln Ser Ala Thr Tyr
140                 145                 150                 155 ctt tct ggc ctg agt ggt gga tca tgg ctc gtt ggc tca atc tac atc       946
Leu Ser Gly Leu Ser Gly Gly Ser Trp Leu Val Gly Ser Ile Tyr Ile
                160                 165                 170 aac aac ttt act act atc tct gcg ctg cag aca cac caa aag ggc acc       994
Asn Asn Phe Thr Thr Ile Ser Ala Leu Gln Thr His Gln Lys Gly Thr
                175                 180                 185 gtt tgg caa ttt cag aat tca ata ttc gaa ggt ccc gat ggg ggc agc      1042
Val Trp Gln Phe Gln Asn Ser Ile Phe Glu Gly Pro Asp Gly Gly Ser
            190                 195                 200 att cag att ttg gat tca gca tcc tat tat aag gac atc agc aat gcg     1090
Ile Gln Ile Leu Asp Ser Ala Ser Tyr Tyr Lys Asp Ile Ser Asn Ala
    205                 210                 215 gtg tcc gga aag gcg gat gcg ggc tac cca act tcc atc act gac tac     1138
Val Ser Gly Lys Ala Asp Ala Gly Tyr Pro Thr Ser Ile Thr Asp Tyr
220                 225                 230                 235 tg  gtactgatag tcgtcggtct tctttgtcgc tacataacat gctgatgatt tcacag    1196
Trp g ggc cgt gct ttg tcc tac cag ctg atc aat gca acc aac ggt ggt cct    1245
  Gly Arg Ala Leu Ser Tyr Gln Leu Ile Asn Ala Thr Asn Gly Gly Pro
```

```
                      240                 245                 250
agc tat aca tgg tcc tcc att gcg cta acc gac aca ttt cag cag gca       1293
Ser Tyr Thr Trp Ser Ser Ile Ala Leu Thr Asp Thr Phe Gln Gln Ala
        255                 260                 265 gag atg ccg atg cct gta gtt gtt gca gat ggt cgc tac ccc gga gaa       1341
Glu Met Pro Met Pro Val Val Val Ala Asp Gly Arg Tyr Pro Gly Glu
270                 275                 280 ctt att atc agc agc aat gcc acc atc tat gaa ttt aat cct tgg gaa       1389
Leu Ile Ile Ser Ser Asn Ala Thr Ile Tyr Glu Phe Asn Pro Trp Glu
285                 290                 295                 300 ttt gga acc ttt gac ccc aca gtt ttt gga ttt gcc cct ctt gag tat       1437
Phe Gly Thr Phe Asp Pro Thr Val Phe Gly Phe Ala Pro Leu Glu Tyr
        305                 310                 315 ctt ggc acc aaa ttc aat gga ggc tca gtt ccg agt aat gag agc tgt       1485
Leu Gly Thr Lys Phe Asn Gly Gly Ser Val Pro Ser Asn Glu Ser Cys
        320                 325                 330 gtg cgc ggc ttt gac aat gcg ggc ttc gtc atg ggt aca tcc tct act       1533
Val Arg Gly Phe Asp Asn Ala Gly Phe Val Met Gly Thr Ser Ser Thr
        335                 340                 345 ctc ttc aat cag ttc ctt ctt cag atc aac tct acg gct ttg ccg gat       1581
Leu Phe Asn Gln Phe Leu Leu Gln Ile Asn Ser Thr Ala Leu Pro Asp
        350                 355                 360 tgg ctg aaa tcc atc ttc acg gac atc ctg agg gac atc ggc gaa aag       1629
Trp Leu Lys Ser Ile Phe Thr Asp Ile Leu Arg Asp Ile Gly Glu Lys
365                 370                 375                 380 gat gag gac att gct cta tac gcg ccc aac cca ttc tac cac tat tcc       1677
Asp Glu Asp Ile Ala Leu Tyr Ala Pro Asn Pro Phe Tyr His Tyr Ser
                385                 390                 395 aac aat acc aac ccc aat gcc cct caa tct gaa ctg gac ctg gtg gac       1725
Asn Asn Thr Asn Pro Asn Ala Pro Gln Ser Glu Leu Asp Leu Val Asp
        400                 405                 410 ggt ggt gaa gat ctg caa aac ata ccg ctg cac cca ttg atc cag cca       1773
Gly Gly Glu Asp Leu Gln Asn Ile Pro Leu His Pro Leu Ile Gln Pro
        415                 420                 425 gag cgt cat gtc gat gtt atc ttc gcc gtt gat tcc tct gcc gat acc       1821
Glu Arg His Val Asp Val Ile Phe Ala Val Asp Ser Ser Ala Asp Thr
        430                 435                 440 aag tac agc tgg ccc aac ggc act gcc ctt gtt gct act tat gag cgt       1869
Lys Tyr Ser Trp Pro Asn Gly Thr Ala Leu Val Ala Thr Tyr Glu Arg
445                 450                 455                 460 agc ctg aac aca tca ggc atc gct aat ggc acc tcc ttt cct gca att       1917
Ser Leu Asn Thr Ser Gly Ile Ala Asn Gly Thr Ser Phe Pro Ala Ile
                465                 470                 475 ccc gat cag gat acg ttc gtg aac gaa ggc ctg aac act cga ccc acg       1965
Pro Asp Gln Asp Thr Phe Val Asn Glu Gly Leu Asn Thr Arg Pro Thr
        480                 485                 490 ttc ttc ggg tgc aac agc tca aac atg acg ggc cca tcg ccc ttg att       2013
Phe Phe Gly Cys Asn Ser Ser Asn Met Thr Gly Pro Ser Pro Leu Ile
        495                 500                 505 gta tat ctc cca aac tat ccc tac acc gct tac tcc aac ttt tct acc       2061
Val Tyr Leu Pro Asn Tyr Pro Tyr Thr Ala Tyr Ser Asn Phe Ser Thr
        510                 515                 520 ttc cag cca gac tac aca gaa gaa gag cga gat gct acc atc ctc aac       2109
Phe Gln Pro Asp Tyr Thr Glu Glu Glu Arg Asp Ala Thr Ile Leu Asn
525                 530                 535                 540 gga tat gat gtg gtg aca atg ggt aac agc act cgt gat ggc aac tgg       2157
Gly Tyr Asp Val Val Thr Met Gly Asn Ser Thr Arg Asp Gly Asn Trp
                545                 550                 555 tca acc tgc gtt ggc tgt gcc atc ttg agt cgg tct ttc gaa cgc aca       2205
Ser Thr Cys Val Gly Cys Ala Ile Leu Ser Arg Ser Phe Glu Arg Thr
```

```
                    560                 565                 570
aac act aat gtg ccg gaa atc tgc aaa caa tgt ttc cag agg tat tgc    2253
Asn Thr Asn Val Pro Glu Ile Cys Lys Gln Cys Phe Gln Arg Tyr Cys
            575                 580                 585 tgg gac ggc tct atc aac aac acc act cct gcg gtt tac gaa ccg gtc    2301
Trp Asp Gly Ser Ile Asn Asn Thr Thr Pro Ala Val Tyr Glu Pro Val
        590                 595                 600 acg att ttg gat agc gca ggc tcc ggg atc ttt cca agt att ctc gct    2349
Thr Ile Leu Asp Ser Ala Gly Ser Gly Ile Phe Pro Ser Ile Leu Ala
605                 610                 615                 620 gct gca atg gct gct att gtt gcc tct tgg act att cta tagaattcat     2398
Ala Ala Met Ala Ala Ile Val Ala Ser Trp Thr Ile Leu
                625                 630 ttcgagagtt tcgcgaaatg tctatttcgg cctgattcta tgctgactga gctgtatcta  2458
cccgtcacaa cttttgtcag aagccatgtt tgtccatttg gaaatttgac gagcaatatt  2518
gtcgttggat ctatctatct atcgctttgt atccctcttg tatatagctt atgcacgaaa  2578
ataaaatatc atggccatga catcccttca ggcgcaatca attacatata agctgggggt  2638
cattaaaatg ccacgtgacg gtggggtccg agtgttgcta tgacaacatc cacgtgactt  2698
ctcaaacaag aaacttaagc acaaacgccg cagctctagc gggcggccaa acgcaacaac  2758
aacacatatc taatcaacaa gctaggtctt cttaagccac agcaaagccc ctgcttgaaa  2818
gctt                                                               2822

<210> SEQ ID NO 2
<211> LENGTH: 633
<212> TYPE: PRT
<213> ORGANISM: Aspergillus fumigatus

<400> SEQUENCE: 2

Met Lys Ser Ile Ala Val Ala Cys Ala Val Ala Gly Leu Leu Leu Ser
1               5                   10                  15

Gly Ala Ser Gly Ala Pro Glu Pro Phe His Gly Glu Ile Leu Gln Arg
            20                  25                  30

Ala Leu Pro Asn Ala Pro Asp Gly Tyr Thr Pro Ser Thr Val Gly Cys
        35                  40                  45

Pro Ala Ser Arg Pro Thr Ile Arg Ser Ala Ala Lys Leu Ser Pro Asn
    50                  55                  60

Glu Thr Ser Trp Leu Gln Thr Arg Arg Gly Lys Thr Thr Ser Ala Met
65                  70                  75                  80

Lys Asp Phe Phe Ser His Val Lys Ile Gln Asp Phe Asp Ala Val Gly
                85                  90                  95

Tyr Ile Asp Arg His Ser Ser Asn Ser Ser Asp Leu Pro Asn Ile Gly
            100                 105                 110

Ile Ala Ile Ser Gly Gly Gly Tyr Arg Ala Leu Met Asn Gly Ala Gly
        115                 120                 125

Ala Ile Lys Ala Phe Asp Ser Arg Thr Pro Asn Ser Thr Ser Pro Gly
    130                 135                 140

Gln Leu Gly Gly Leu Leu Gln Ser Ala Thr Tyr Leu Ser Gly Leu Ser
145                 150                 155                 160

Gly Gly Ser Trp Leu Val Gly Ser Ile Tyr Ile Asn Asn Phe Thr Thr
                165                 170                 175

Ile Ser Ala Leu Gln Thr His Gln Lys Gly Thr Val Trp Gln Phe Gln
            180                 185                 190

Asn Ser Ile Phe Glu Gly Pro Asp Gly Ser Ile Gln Ile Leu Asp
        195                 200                 205
```

```
Ser Ala Ser Tyr Tyr Lys Asp Ile Ser Asn Ala Val Ser Gly Lys Ala
    210                 215                 220

Asp Ala Gly Tyr Pro Thr Ser Ile Thr Asp Tyr Trp Gly Arg Ala Leu
225                 230                 235                 240

Ser Tyr Gln Leu Ile Asn Ala Thr Asn Gly Gly Pro Ser Tyr Thr Trp
                245                 250                 255

Ser Ser Ile Ala Leu Thr Asp Thr Phe Gln Gln Ala Glu Met Pro Met
            260                 265                 270

Pro Val Val Ala Asp Gly Arg Tyr Pro Gly Glu Leu Ile Ile Ser
        275                 280                 285

Ser Asn Ala Thr Ile Tyr Glu Phe Asn Pro Trp Glu Phe Gly Thr Phe
    290                 295                 300

Asp Pro Thr Val Phe Gly Phe Ala Pro Leu Glu Tyr Leu Gly Thr Lys
305                 310                 315                 320

Phe Asn Gly Gly Ser Val Pro Ser Asn Glu Ser Cys Val Arg Gly Phe
                325                 330                 335

Asp Asn Ala Gly Phe Val Met Gly Thr Ser Thr Leu Phe Asn Gln
            340                 345                 350

Phe Leu Leu Gln Ile Asn Ser Thr Ala Leu Pro Asp Trp Leu Lys Ser
        355                 360                 365

Ile Phe Thr Asp Ile Leu Arg Asp Ile Gly Glu Lys Asp Glu Asp Ile
    370                 375                 380

Ala Leu Tyr Ala Pro Asn Pro Phe Tyr His Tyr Ser Asn Asn Thr Asn
385                 390                 395                 400

Pro Asn Ala Pro Gln Ser Glu Leu Asp Leu Val Asp Gly Gly Glu Asp
                405                 410                 415

Leu Gln Asn Ile Pro Leu His Pro Leu Ile Gln Pro Glu Arg His Val
            420                 425                 430

Asp Val Ile Phe Ala Val Asp Ser Ser Ala Asp Thr Lys Tyr Ser Trp
        435                 440                 445

Pro Asn Gly Thr Ala Leu Val Ala Thr Tyr Glu Arg Ser Leu Asn Thr
    450                 455                 460

Ser Gly Ile Ala Asn Gly Thr Ser Phe Pro Ala Ile Pro Asp Gln Asp
465                 470                 475                 480

Thr Phe Val Asn Glu Gly Leu Asn Thr Arg Pro Thr Phe Phe Gly Cys
                485                 490                 495

Asn Ser Ser Asn Met Thr Gly Pro Ser Pro Leu Ile Val Tyr Leu Pro
            500                 505                 510

Asn Tyr Pro Tyr Thr Ala Tyr Ser Asn Phe Ser Thr Phe Gln Pro Asp
        515                 520                 525

Tyr Thr Glu Glu Glu Arg Asp Ala Thr Ile Leu Asn Gly Tyr Asp Val
    530                 535                 540

Val Thr Met Gly Asn Ser Thr Arg Asp Gly Asn Trp Ser Thr Cys Val
545                 550                 555                 560

Gly Cys Ala Ile Leu Ser Arg Ser Phe Glu Arg Thr Asn Thr Asn Val
                565                 570                 575

Pro Glu Ile Cys Lys Gln Cys Phe Gln Arg Tyr Cys Trp Asp Gly Ser
            580                 585                 590

Ile Asn Asn Thr Thr Pro Ala Val Tyr Glu Pro Val Thr Ile Leu Asp
        595                 600                 605

Ser Ala Gly Ser Gly Ile Phe Pro Ser Ile Leu Ala Ala Ala Met Ala
    610                 615                 620

Ala Ile Val Ala Ser Trp Thr Ile Leu
```

-continued

```
<210> SEQ ID NO 3
<211> LENGTH: 18
<212> TYPE: PRT
<213> ORGANISM: Aspergillus fumigatus

<400> SEQUENCE: 3

Asp Ser Ala Ser Tyr Tyr Lys Asp Tyr Ser Asn Ala Val Ser Gly Lys
1               5                   10                  15

Ala Asp

<210> SEQ ID NO 4
<211> LENGTH: 18
<212> TYPE: PRT
<213> ORGANISM: Aspergillus fumigatus
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (16)..(16)
<223> OTHER INFORMATION: Any amino acid

<400> SEQUENCE: 4

Ala Leu Pro Asn Ala Pro Asp Gly Tyr Thr Pro Ser Xaa Val Gly Xaa
1               5                   10                  15

Pro Ala

<210> SEQ ID NO 5
<211> LENGTH: 5
<212> TYPE: PRT
<213> ORGANISM: Aspergillus fumigatus

<400> SEQUENCE: 5

Asp Ser Ala Ser Tyr
1               5

<210> SEQ ID NO 6
<211> LENGTH: 10
<212> TYPE: PRT
<213> ORGANISM: Aspergillus fumigatus

<400> SEQUENCE: 6

Pro Val Val Val Ala Asp Gly Asn Tyr Pro
1               5                   10

<210> SEQ ID NO 7
<211> LENGTH: 10
<212> TYPE: PRT
<213> ORGANISM: Aspergillus fumigatus
<220> FEATURE:
<221> NAME/KEY: MOD_RES
<222> LOCATION: (1)..(1)
<223> OTHER INFORMATION: Any amino acid

<400> SEQUENCE: 7

Xaa Thr Ser Ser Thr Leu Phe Asn Gln Phe
1               5                   10

<210> SEQ ID NO 8
<211> LENGTH: 19
<212> TYPE: PRT
<213> ORGANISM: Aspergillus fumigatus

<400> SEQUENCE: 8
```

-continued

Lys Asp Phe Phe Ser His Val Lys Ile Gln Asp Phe Asp Ala Val Gly
1               5                   10                  15

Tyr Ile Asp

<210> SEQ ID NO 9
<211> LENGTH: 5
<212> TYPE: PRT
<213> ORGANISM: Aspergillus fumigatus

<400> SEQUENCE: 9

Ala Leu Pro Asn Ala
1               5

<210> SEQ ID NO 10
<211> LENGTH: 14
<212> TYPE: PRT
<213> ORGANISM: Aspergillus fumigatus
<220> FEATURE:
<221> NAME/KEY: MOD_RES
<222> LOCATION: (12)..(12)
<223> OTHER INFORMATION: Any amino acid

<400> SEQUENCE: 10

Asn Thr Ala Thr Ala Ile Lys Ala Phe Asp Ser Xaa Thr Pro
1               5                   10

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gactcgagtc gacatcgatt tttttttttt tttttttv                           39

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gactttgacg ctgtggggta catcga                                        26

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tcaaaagcct tgattgcggt agcagtgttc at                                 32

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 14
ctttgcggca ctgcgaat                                                     18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atatttgatc ttattgtc                                                     18

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggcgcaggtg cgattaaggc ttttga                                            26

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ttcgcgaaac tctcgaaatg aattcta                                           27

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cgcggatccg tcatgaagtc catcgcagtg gcgtgc                                 36

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ttgactagtt tgaaccacac ttcaag                                            26

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
```

-continued

```
gaattctggt gttttgatct ttt                                      23

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agcaccgcta gcaccggaca ataataggcc ggcgac                        36

<210> SEQ ID NO 22
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tccggtgcta gcggtgctgc cctgcccaat gccccgatg gatacaca            48

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gaagtccttc atcgcagaag t                                        21

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctgatattta cgtaaaaatc gtca                                     24

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cttgcctcga cgcgtctgaa gccatga                                  27
```